United States Patent [19]
Kochanek et al.

[11] Patent Number: 5,981,225
[45] Date of Patent: Nov. 9, 1999

[54] GENE TRANSFER VECTOR, RECOMBINANT ADENOVIRUS PARTICLES CONTAINING THE SAME, METHOD FOR PRODUCING THE SAME AND METHOD OF USE OF THE SAME

[75] Inventors: Stefan Kochanek; Gudrun Schiedner, both of Cologne, Germany

[73] Assignee: Baylor College of Medicine, Houston, Tex.

[21] Appl. No.: 09/060,828

[22] Filed: Apr. 16, 1998

[51] Int. Cl.⁶ .............................. C12P 21/00; C12N 7/01; C12N 15/12; C12N 15/33
[52] U.S. Cl. ..................... 435/69.1; 435/456; 435/457; 435/320.1; 536/23.5; 536/23.72; 536/24.1
[58] Field of Search ................... 435/69.1, 456, 435/457, 320.1; 536/23.5, 23.72, 24.1

[56] References Cited

U.S. PATENT DOCUMENTS 5,670,488 9/1997 Gregory ................................. 514/44

FOREIGN PATENT DOCUMENTS

WO 94/28152 12/1994 WIPO.
WO 9613597 5/1996 WIPO.
WO 9700326 1/1997 WIPO.

OTHER PUBLICATIONS

Bett et al. Packaging capacity and stability of human adenovrus type 5 vectors. J. Virology vol. 67 pp. 5911–5921, 1993.
Karpati et al, *Clin. Invest. Med.*, 17(5):499–509 (1994).
Deuring et al, *Proc. Natl. Acad. Sci., USA*, 78(5):3142–3146 (1981).
Culver et al, *TIG*, 10(5):174–178 (1995).
Miller et al, *The FASEB Journal*, 9:190–199 (1995).
Hodgson, *Exp. Opin. Ther. Patents*, 5(5):459–468 (1995).
Marshall, *Science*, 269:1050–1055 (1995).
Gilardi et al, *FEBS*, 267(1):60–62 (1990).
Amalfitano et al, *American Journal of Human Genetics*, 57(4 Suppl.):A234 (1995).
Berkner, *Biotechniques*, 6(7):617 (1988).
Clemens et al, *Gene Therapy*, 3:965–972 (1996).
Chen et al, *Proc. Natl. Acad. Sci., USA*, 94:000–000 (1–6) (1997).
Kochanek et al, *Proc. Natl. Acad. Sci., USA*, 93:5731–5736 (1996).
Mitani et al, *Proc. Natl. Acad. Sci., USA*, 92:3854–3858 (1995).
Parks et al, *Journal of Virology*, 71(4):3293–3298 (1997).
Boulikas, *International Review of Scitology*, 162A:279–338 (1995?).
Sykes et al, *Mol. Gen. Genet.*, 212:301–309 (1988).

*Primary Examiner*—John S. Brusca
*Attorney, Agent, or Firm*—Sughrue, Mion, Zinn, Macpeak & Seas, PLLC

[57] ABSTRACT

A gene transfer vector comprising adenovirus inverted terminal repeats, at least one adenovirus packaging signal, and an adenoviral VAI gene and/or VAII gene; recombinant adenovirus particles containing the same; a method for producing the same and a method of use of the same to introduce and express a foreign gene in adenovirus target cells, is disclosed.

36 Claims, 4 Drawing Sheets

FIGURE 1

*CATCATCAAT AATATACCTT ATTTTGGATT GAAGCCAATA TGATAATGAG GGGGTGGAGT*

*TTGTGACGTG GCGCGGGGCG TGGGAACGGG GCGGGTGACG TAGTAGTGTG GCGGAAGTGT*

GATGTTGCAA GTGTGGCGGA ACACATGTAA GCGACGGATG TGGCAAAAGT GACGTTTTG

GTGTGCGCCG GTGTACACAG GAAGTGACAA TTTTCGCGCG GTTTTAGGCG GATGTTGTAG

TAAATTTGGG CGTAACCGAG TAAGATTTGG CCATTTTCGC GGGAAAACTG AATAAGAGGA

AGTGAAATCT GAATAATTTT GTGTTACTCA TAGCGCGTAA TGTTTGTCTA GGGCCGCGGG

ACTTTGACCG TTTACGTGGA GACTCGCCCA GGTGTTTTC TCAGGTGTTT TCCGCGTTCC

GGGTCAAAGT TGGCGTTTTA TTATTATAGT CAGCTGACGT GTAGTGTATTT ATACCCGG

FIGURE 2

GGGCACTCTT CCGTGGTCTG GTGGATAAAT TCGCAAGGGT ATCATGGCGG ACGACCGGGG

TTCGAACCCC GGATCCGGCC GTCCGCCGTG ATCCATGCGG TTACCGCCCG CGTGTCGAAC

CCAGGTGTGC GACGTCAGAC AACGGGGGAG CGCTCCTTTT GGCTTCCTTC CAGGCGCGGC

GGCTGCTGCG CTAGCTTTTT TGGCCACTGG CCGCGCGCGG CGTAAGCGGT TAGGCTGGAA

AGCGAAAGCA TTAAGTGGCT CGCTCCCTGT AGCCGGAGGG TTATTTTCCA AGGGTTGAGT

CGCAGGACCC CCGGTTCGAG TCTCGGGCCG GCCGGACTGC GGCGAACGGG GGTTTGCCTC

CCCGTCATGC AAGACCCCGC TTGCAAATTC CTCCGGAAAC AGGGACGAGC CCCTTT

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE: DNA (iii) HYPOTHETICAL: NO (vi) ORIGINAL SOURCE:
        (A) ORGANISM: Adenovirus type 5

(xi) SEQUENCE DESCRIPTION: SEQ ID NO:1:

```
CATCATCAAT AATATACCTT ATTTTGGATT GAAGCCAATA TGATAATGAG GGGGTGGAGT      60

TTGTGACGTG GCGCGGGGCG TGGGAACGGG GCGGGTGACG TAGTAGTGTG GCGGAAGTGT     120

GATGTTGCAA GTGTGGCGGA ACACATGTAA GCGACGGATG TGGCAAAAGT GACGTTTTTG     180

GTGTGCGCCG GTGTACACAG GAAGTGACAA TTTTCGCGCG GTTTTAGGCG GATGTTGTAG     240

TAAATTTGGG CGTAACCGAG TAAGATTTGG CCATTTTCGC GGGAAAACTG AATAAGAGGA     300

AGTGAAATCT GAATAATTTT GTGTTACTCA TAGCGCGTAA TATTTGTCTA GGGCCGCGGG     360

ACTTTGACCG TTTACGTGGA GACTCGCCCA GGTGTTTTTC TCAGGTGTTT TCCGCGTTCC     420

GGGTCAAAGT TGGCGTTTTA TTATTATAGT CAGCTGACGT GTAGTGTATTT ATACCCGG     479
```

(2) INFORMATION FOR SEQ ID NO:2:

(i) SEQUENCE CHARACTERISTICS:
        (A) LENGTH: 416 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Adenovirus type 2

(xi) SEQUENCE DESCRIPTION: SEQ ID NO:2:

```
GGGCACTCTT CCGTGGTCTG GTGGATAAAT TCGCAAGGGT ATCATGGCGG ACGACGGGG      60

TTCGAACCCC GGATCCGGCC GTCCGCCGTG ATCCATGCGG TTACCGCCCG CGTGTCGAAC    120
```

```
CCAGGTGTGC GACGTCAGAC AACGGGGAG CGCTCCTTTT GGCTTCCTTC CAGGCGCGGC       180

GGCTGCTGCG CTAGCTTTTT TGGCCACTGG CCGCGCGCGG CGTAAGCGGT TAGGCTGGAA       240

AGCGAAAGCA TTAAGTGGCT CGCTCCCTGT AGCCGGAGGG TTATTTTCCA AGGGTTGAGT       300

CGCAGGACCC CCGGTTCGAG TCTCGGGCCG GCCGGACTGC GGCGAACGGG GGTTTGCCTC       360

CCCGTCATGC AAGACCCCGC TTGCAAATTC CTCCGGAAAC AGGGACGAGC CCCTTT          416
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:3:

```
GGCGCGCCCC TAGGGGCCGG CCTTAATTAA                                      30
```

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:4:

```
TTAATTAAGG CCGGCCCCTA GGGGCGCGCC                                      30
```

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:5:

```
ATTTAAATGC CGCCCGTTT AAACTACGTA                                       30
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:6:

TACGTAGTTT AAACGGGCGG GCATTTAAAT                                              30

(2) INFORMATION FOR SEQ ID NO:7:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:7:

TTCGAACTAA TCGAGTATAC ATTCGTAGGG ATCCGATGTC CGATTTAAAT                        50

(2) INFORMATION FOR SEQ ID NO:8:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:8:

ATTTAAATCG GACATCGGAT CCCTACGAAT GTATACTCGA TTAGTTCGAA                        50

(2) INFORMATION FOR SEQ ID NO:9:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:9:

GGATAAACAT CCCC                                                              14

(2) INFORMATION FOR SEQ ID NO:10:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:10:

GGGGATGTTT ATCC                                                14

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:11:

TTAACCGGAC TGCGGCGAAC GG                                       22

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:12:

TTAATTTTCC GCCATGATAC CCTTGCGA                                 28

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:13:

CGGCGGATCC ATTTAAAT                                            18

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:14:

ATTTAAATGG ATCCGCC                                             17

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:15:

TTCGAATTTA AATCATCATC AATAATATAC CTTATTTTG            39

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:16:

TGATCTAGAC GCTATGAGTA ACACAAA                    27

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:17:

AGCTTTGTTT AAACATCATC AATAATATAC CTTATTTTG            39

(2) INFORMATION FOR SEQ ID NO:18:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:18:

CGATAAGCTT GATATCAAAA CGCCAACTTT GACCC              35

(2) INFORMATION FOR SEQ ID NO:19:

(i) SEQUENCE CHARACTERISTICS:
        (A) LENGTH: 36 base pairs

-continued

```
    (B) TYPE: nucleic acid
    (C) STRANDEDNESS: single
    (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:19:

CGATAAGCTT GATATCACTC CGCCCTAAAA CCTACG                        36
```

GENE TRANSFER VECTOR, RECOMBINANT ADENOVIRUS PARTICLES CONTAINING THE SAME, METHOD FOR PRODUCING THE SAME AND METHOD OF USE OF THE SAME

The invention described herein was developed with support from the U.S. government under Grant No. NIH HL 51754. The government has certain rights to this invention.

FIELD OF THE INVENTION

The present invention relates to a gene transfer vector comprising adenovirus inverted terminal repeats, at least one adenovirus packaging signal, and an adenoviral VAI gene and/or VAII gene; recombinant adenovirus particles containing the same; a method for producing the same and a method of use of the same to introduce and express a foreign gene in adenovirus target cells.

BACKGROUND OF THE INVENTION

I. Adenovirus Vectors

Adenoviruses have attracted increasing attention as expression vectors, especially for human gene therapy (Berkner, *Curr. Top. Microbiol. Immunol.*, 158:39–66 (1992)). This is because the virus particle is relatively stable, and can be prepared as a high titer stock ($10^9$ plaque forming units/ml) without purification. In addition, adenoviruses are useful because they can infect non-replicating cells. Further, adenovirus vectors have been proven safe and effective in humans. However, the following limitations have prevented their general use:

(1) The expression of adenovirus proteins in infected cells is believed to trigger a cellular immune response that precludes long-term expression of the transferred gene (Stratford-Perricaudet et al, *Hum. Gene Ther.*, 1:241 (1990); Ginsberg et al, *Proc. Natl. Acad. Sci., USA*, 88:1651 (1991); Yang et al, *Proc. Natl. Acad. Sci., USA*, 91:4407 (1994); Dai et al, *Proc. Natl. Acad. Sci., USA*, 92:1401 (1995); Jaffe et al, *Nat. Genet.*, 1:372 (1992); Li et al, *Hum. Gene Ther.*, 4:403 (1993); Engelhardt et al, *Hum. Gene Ther.*, 4:759 (1993); Simon et al, *Hum. Gene Ther.*, 4:771 (1993); and Smith et al, *Nat. Genet.*, 5:397 (1993)); and (2) The insert capacity of currently available adenovirus vectors is limited to about 8.0 kb of foreign DNA (Bett et al, *Proc. Natl. Acad. Sci., USA*, 13:8802 (1994)).

Hence, broad application of in vivo gene transfer for the treatment of inherited or acquired diseases requires a substantial improvement of existing systems, or the development of new viral or non-viral vector systems.

A. Reduction of Immunogenicity

In order to reduce the expression of adenovirus proteins, and thus reduce immunogenicity, and in order to prevent viral replication, the current adenovirus vectors have deletions in the E1 and/or E3 regions of the adenovirus genome. All of the other essential viral proteins are encoded by the adenovirus vector itself. E1 proteins can be complemented by culturing the E1 adenoviruses in human 293 cells. The E3 region is dispensable for growth of the virus in vitro.

Recent efforts have been directed at the deletion of additional regions (E2, E4) of the adenovirus genome, which encode early viral functions, in an attempt to further reduce viral gene expression after transduction of the target cells with the adenovirus vector (Engelhardt et al, *Proc. Natl. Acad. Sci., USA*, 91:6196 (1994); Yang et al, *Nature Genet.*, 7:362 (1994); Zhou et al, Gene Therapy and Molecular Medicine, Keystone Symposia on Molecular and Cellular Biology, Steamboat Springs, Colo., Mar. 26–Apr. 1, 1995; Perricaudet et al, Ibid; and Finer et al, Ibid). To propagate these adenovirus vectors, cell lines have been developed that can provide the deleted functions. However, theoretically, it is very difficult, if not impossible, to provide all of the deleted adenovirus functions by a complementing cell line without substantially compromising the high adenovirus titer, which is currently one of the major advantages of adenovirus vectors.

B. Increasing the Capacity of Adenoviruses to Carry Foreign Genes

The lower packaging limit of adenovirus is unknown. However, the upper packaging limit of Ad5 is approximately 38 kb (Bett et al, *J. Virol.*, 67:5911–5921 (1993)). As a result, adenovirus vectors with deletions of both the E1 and E3 sequences, about 6.0 kb in total, have a capacity for insertion of foreign DNA of up to approximately 8.0 kb.

After repeated passaging of permissive cells infected at a high multiplicity of infection (hereinafter "m.o.i.") with different adenovirus serotypes, subgenomic DNAs preferentially containing the left end of the adenovirus genome are packaged into adenovirus particles, and can be partially separated from wild-type adenovirus particles by cesium chloride (CsCl) density gradient centrifugation (Hammarskjold et al, *Cell*, 20:787–795 (1980)). In addition, after repeated passaging of permissive human KB cells infected at a high m.o.i. with Ad12, hybrid viruses containing symmetrically duplicated chromosomal DNA of the KB cell line flanked by a 700–1150 bp DNA fragment from the left terminus of Ad12 are produced (Deuring et al, *Proc. Natl. Acad. Sci., USA*, 78:3142–3146 (1981); Doerfler, *Curr. Top. Microbiol. Immunol.*, 101:127–193 (1982); and Deuring et al, *Gene*, 26:283–289 (1983)). These hybrid viruses can be partially separated from Ad12 by CsCl equilibrium density gradient, and also can be propagated over years together with Ad12. However, the purity of these particles appears to be very low.

SV40/Ad5 hybrid viruses containing a total of 35 kb which comprise 5.5 copies of the SV40 genome and only 3.5 kb DNA from the left end of Ad5 have also been reported (Gluzman et al, *J. Virol.*, 45:91–103 (1983)). The smallest genome size among the different types of Ad5/SV40 hybrid viruses is about 25 kb (Hassell et al, *J. Mol. Biol.*, 120:209–247 (1978)).

It has recently been determined that the sequences required in cis for replication and packaging of adenovirus DNA comprise less than 500 bp (Grable et al, *J. Virol.*, 64:2047–2056, (1990); and Hearing et al, *J. Virol.*, 61:2555–2558 (1987)).

All of the cis-elements for packaging and replication are contained in 380 bp from the left end of the genome and 103 bp from the right end of the genome (Sussenbach et al, In: *Current Topics in Microbiology and Immunology*, Vol. 109, Doerfler, Ed. Springer-Verlag, Berlin, pp. 53–73 (1983); Tamanoi et al, In: *Current Topics in Microbiology and Immunology*, Vol. 109, Doerfler, Ed. Springer-Verlag, Berlin, pp 75–87 (1983); Hearing et al, supra; and Grable et al, supra).

It was postulated in the present invention that an adenovirus vector could be prepared in which all of the regions of the adenovirus genome were deleted, except for the packaging signal, and the inverted terminal repeats, containing the replication signal. Thus, it was postulated in the present invention that it is possible to accommodate up to 37 kb of foreign DNA into defective adenovirus vectors by supplying all of the proteins in trans from a helper virus or cell line. As a result, it was postulated in the present invention that it would be possible to deliver multiple or large genes containing tissue-specific or inducible promoters, as well as marker genes, in one vector, in cis. Such a vector would not encode any viral proteins, and thus would not be toxic or immunogenic to the host. Hence, the above-discussed problem of the immune response of the host arising from expression of viral proteins from the known adenovirus vectors might also be diminished.

Helper-dependent adenovirus vectors encoding the SV40 T antigen have been previously reported (Mansour et al, Proc. Natl. Acad. Sci., USA, 82:1359–1363 (1985); and Yamada et al, Proc. Natl. Acad. Sci., USA, 82:3567–3571 (1985)). However, these vectors, which were used to overproduce the polyoma T antigens (Mansour et al, supra) and the HSV thymidine kinase gene (Yamada et al, supra), had to be selected for by their growth in monkey cells. The T antigen provides a helper function, which overcomes the block to adenovirus growth in simian cells. However, since the T antigen of the tumor virus, SV40, is able to transform cells to a cancerous state (Hunter, Sci. Amer., 251:70–79 (1994)), it cannot be used in any application in humans.

It was postulated in U.S. patent application Ser. No. 08/488,014, filed Jun. 7, 1995, which is incorporated by reference herein in its entirety, that the use of a selection step could be avoided by a gene transfer vector comprising, in 5' to 3' orientation, the following elements:

(i) a first adenovirus inverted terminal repeat,
(ii) a foreign gene, and
(iii) a second adenovirus inverted terminal repeat, wherein one or both of element (i) and element (iii) additionally comprise an adenovirus packaging signal; and that CsCl centrifugation could be employed to purify recombinant adenovirus containing the same, wherein the recombinant adenovirus is obtained by co-transfection of said gene transfer vector and adenovirus genomic DNA (see also, Mitani et al, Proc. Natl. Acad., Sci., USA, 92:3854–3858 (1995); Kochanek et al, Proc. Natl. Acad., Sci., USA, 93:5731–5736 (1996); and Clemens et al, Gene Therapy, 3:965–972 (1996)).

However, with the above-discussed gene transfer vector, there is the disadvantage in that multiple serial passages are required to obtain sufficient quantities of recombinant adenovirus. This is because the percentage of recombinant adenovirus produced is still a small percentage of the total amount of adenovirus produced upon co-transfection of the gene transfer vector with the adenovirus genomic DNA.

The present invention has overcome the above-described problem, without increasing the immunogenicity of the recombinant virus due to the production of adenovirus proteins, by incorporating into the gene transfer vector an adenovirus VAI gene and/or VAII gene, and the use of adenovirus genomic DNA which has a defective VAI gene and/or VAII gene during co-transfection. The VA genes encode small RNAs of 150–170 nucleotides in length, synthesized by the host RNA polymerase III. Ad2 expresses two VA RNAs, a major species VAI and a minor species VAII—although not all adenoviruses are endowed with two such RNAs (Ma et al, J. Virol. 67: 6605 (1993)). In Ad2 infected cells, VAI and VAII RNAs are expressed in equal amounts early in the infection cycle, whereas in the late phase of infection, the transcription rate of VAI RNA is strongly induced. VA RNAs are very stable and accumulate to high levels, possibly because of their compact secondary structure (Mathews, In: Current Topics in Microbiology and Immunology, Vol. 199, Doerfler and Boehm, Eds. Springer-Verlag, Berlin, pp. 173–187 (1995); and Pruzin et al, In: Current Topics in Microbiology and Immunology, Vol. 199, Doerfler and Boehm, Eds. Springer-Verlag, Berlin, pp. 201–226 (1995)). VAI RNA plays an important role in late viral protein synthesis in adenovirus infected cells (Thimmappaya et al, Cell, 31:543 (1982)). In cells infected with adenovirus having a deletion of the VA genes, initiation of translation of late viral proteins is strongly reduced (Schneider et al, Cell, 37:291 (1984)). VAI RNA binds to interferon and double-stranded RNA inducible eIF-2α kinase, and thus prevents its activation. In its activated form, this kinase inhibits translation by phosphorylation of the translation initiation factor eIF-2α (Thimmappaya et al, supra; Babich et al, Mol. Cell. Biol., 3:1212 (1983); Schneider et al, supra; and Siekierka et al, Proc. Natl. Acad. Sci., USA, 82:1959 (1985)). Thus, adenovirus genomic DNA with defective VA genes alone has poor amplification capacities.

SUMMARY OF THE INVENTION

An object of the present invention is to provide a gene transfer vector that does not induce a host cellular immune response against expressed viral proteins.

An additional object of the present invention is to provide a gene transfer vector that can carry about 36 kb of foreign DNA.

Still another object of the present invention is to provide recombinant adenovirus particles which have encapsidated therein said gene transfer vectors, as well as a method for isolating said recombinant adenovirus particles.

Yet another object of the present invention is to provide a method for introducing and expressing foreign genes in adenovirus target cells.

A further object of the present invention is to provide a method wherein the amount of recombinant adenovirus is enriched vis-a-vis the total amount of adenovirus produced.

These and other objects, which will be apparent from the detailed description of the invention provided hereinafter, have been met in one embodiment, by a gene transfer vector comprising, in 5' to 3' orientation, the following elements:

(i) a first adenovirus inverted terminal repeat,
(ii) an adenoviral VAI gene and/or VAII gene,
(iii) a gene foreign to adenovirus, wherein said gene is operably linked to a promoter functional in adenovirus target cells, and
(iv) a second adenovirus inverted terminal repeat, wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively.

BRIEF DESCRIPTION OF THE DRAWINGS

FIG. 1 shows the DNA sequence of a DNA fragment containing the inverted terminal repeat and full-length packaging signal of Ad5 (SEQ ID NO:1). In FIG. 1, the inverted terminal repeat (nucleotides 1–103) is in italics, and the 5 elements constituting the packaging signal (nucleotides 194–358) are in bold.

FIG. 2 shows the DNA sequence of a DNA fragment containing the VA genes of Ad2 (SEQ ID NO:2). In FIG. 2, the VAI (nucleotides 10609–10766) and the VAII (nucleotides 10866–11025) genes, are in italics.

DETAILED DESCRIPTION OF THE INVENTION

Figure 3:
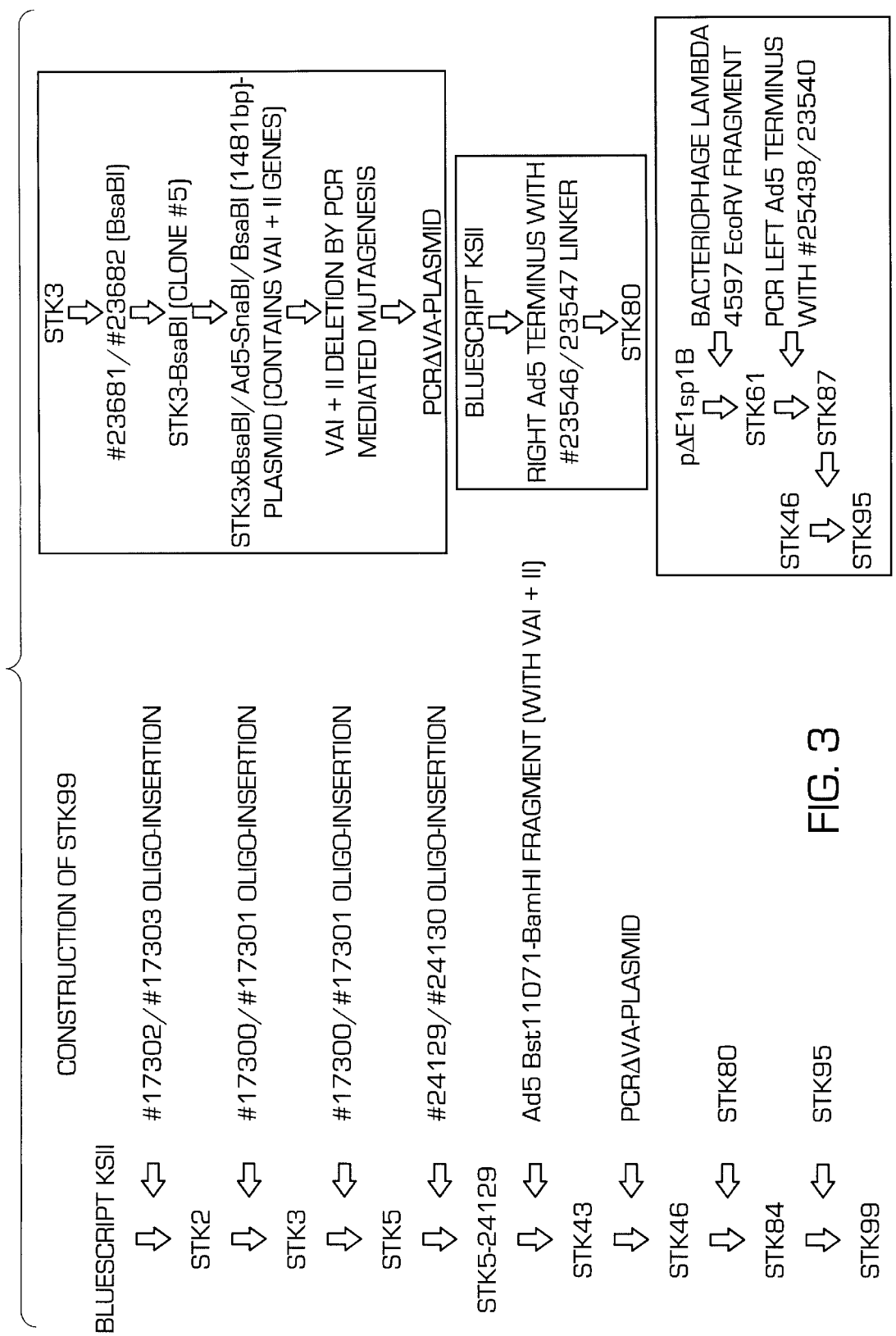
FIG. 3 schematically illustrates the construction of vector STK99.
Figure 4:
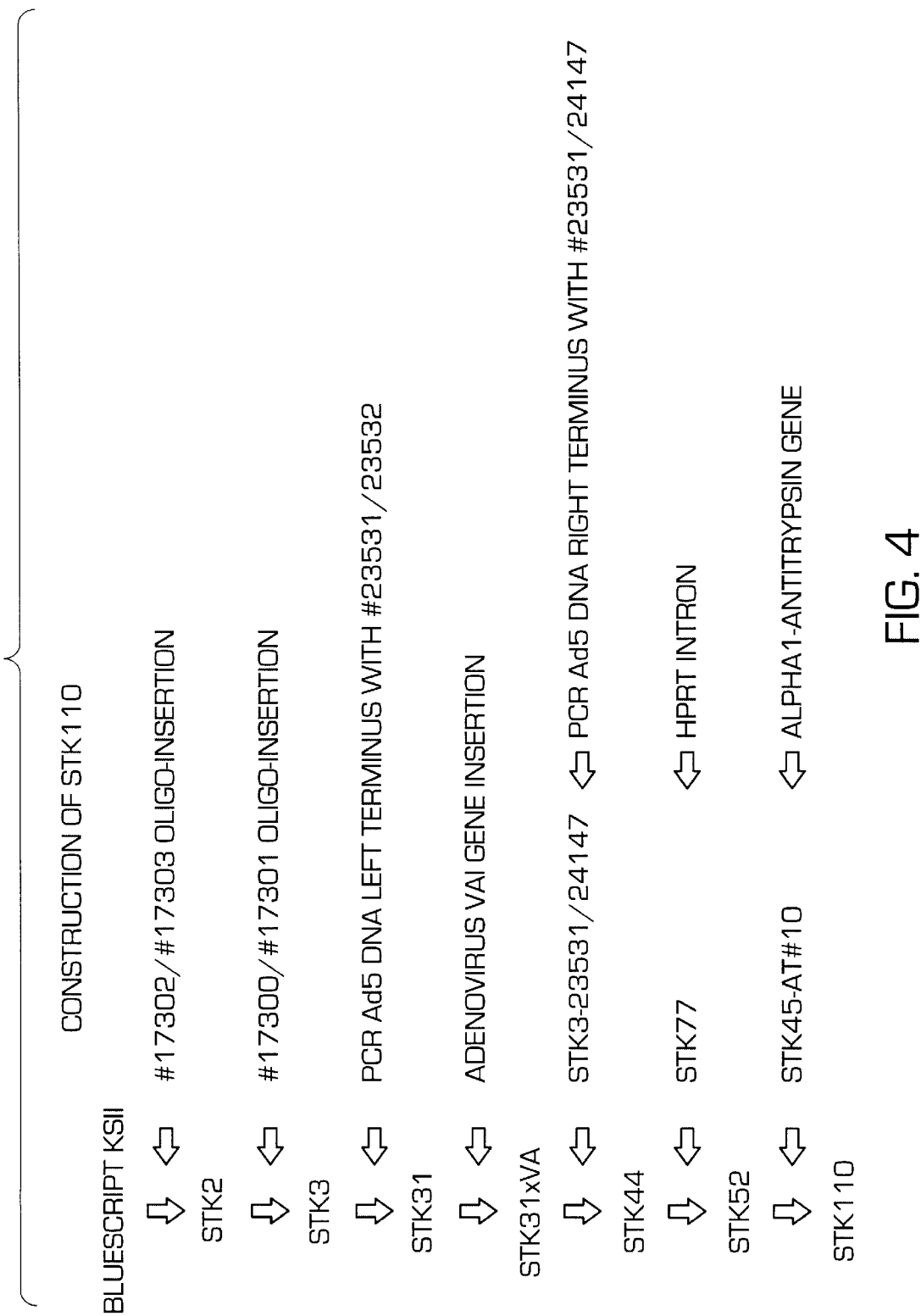
FIG. 4 schematically illustrates the construction of vector STK110.

As discussed above, in one embodiment, the present invention relates to a gene transfer vector comprising, in 5' to 3' orientation, the following elements:

(i) a first adenovirus inverted terminal repeat, (ii) an adenoviral VAI gene and/or VAII gene, (iii) a gene foreign to adenovirus, wherein said gene is operably linked to a promoter functional in adenovirus target cells, and (iv) a second adenovirus inverted terminal repeat, wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively.

The inverted terminal repeats constitute the adenovirus origin of replication.

The particular adenovirus serotype employed in the present invention from which the inverted terminal repeats are derived or based upon, is not critical. Examples of such adenovirus serotypes which can be employed in the present invention are well-known in the art and include more than 40 different human adenovirus serotypes, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: *Adenovirus DNA*, Doerfler, Ed., Martinus Nijhoff Publishing, Boston, pp. 408–441 (1986)), as well as any of the well-known non-human adenovirus, including those isolated from cattle, sheep, pigs and other mammalian species, or isolated from chickens, turkeys and other avian species (Wigand et al, supra).

Adenovirus inverted terminal repeats are about 100–150 bp in length. The length and sequence of the inverted terminal repeats varies with the serotype.

The DNA sequence of the inverted terminal repeat of Ad5 is shown in FIG. 1 (SEQ ID NO:1). It begins at nucleotide 1 and it ends at nucleotide 103.

The DNA sequences of inverted terminal repeats of other adenovirus serotypes, e.g., Ad2, Ad4, Ad5, Ad7, Ad9, Ad12, Ad18, and Ad31, are also well-known in the art (Tamanoi et al, supra).

For those adenovirus serotypes where the DNA sequence of the inverted terminal repeats has not yet been determined, the DNA sequence of the inverted terminal repeat can be readily determined by DNA sequencing (Sambrook et al, In: *Molecular Cloning. A Laboratory Manual*, Cold Spring Harbor Laboratory Press (1989)).

The adenovirus inverted terminal repeats for use in the present invention can be obtained by DNA cloning from adenovirus DNA or chemically synthesized (Sambrook et al, supra).

The packaging signal is required to encapsidate the viral DNA during the late phase of infection into the preformed capsids.

The particular adenovirus serotype employed in the present invention from which the packaging signal is derived or based upon, is not critical. Examples of such adenovirus serotypes which can be employed in the present invention include those exemplified above.

The adenovirus packaging signal is about 100 bp in length. The length and sequence of the packaging signal varies with the serotype.

The DNA sequence of the packaging signal of Ad5 is shown in FIG. 1 (SEQ ID NO:1). The packaging signal begins at nucleotide 241 and ends at nucleotide 375.

The DNA sequences of the packaging signals of other adenovirus serotypes, e.g., Ad3 (Kosturko et al, *J. Virol.*, 43:1132–1137 (1982), Ad16 (Hammarskjold et al, supra), Ad7 and Ad12 (Hearing et al, supra) are also well-known in the art.

The packaging signal in Ad2 or Ad5 consists of 7 short homologous DNA sequences that have the 8 bp consensus sequence (A/T)AN(A/T)TTTG (Grable et al, supra).

For those adenovirus serotypes where the DNA sequence of the packaging signal has not yet been determined, the DNA sequence of the packaging signal can be readily determined by DNA sequencing (Sambrook et al, supra)

The adenovirus packaging signal for use in the present invention can be obtained by DNA cloning from adenovirus DNA or chemically synthesized (Sambrook et al, supra).

As discussed above, the Ad2 VAI and VAII genes encode for RNA of 150–170 nucleotides in length. Both genes are oriented in the same direction and are separated by 100 nucleotides of spacer DNA. The number, length and sequence of the adenovirus VA RNAs varies with the serotype.

The DNA sequence of the VA genes of Ad2 is shown in FIG. 2. VAI RNA begins at nucleotide 10609 and ends at nucleotide 10766, VAII RNA begins at nucleotide 10866 and ends at nucleotide 11025. The DNA sequences of the VA gene(s) of other serotypes, e.g., of subgroups Ad11, Ad12, Ad34, Ad35, simian Ad7 and chicken adenovirus (CELO) with a single VA RNA gene, and subgroups Ad5 and Ad7 with two VA RNA genes are also well-known in the art (Soederlund et al, *Cell*, 7: 585 (1976); Foehring et al, *Virol.*, 95:295 (1979); Larsson et al, *J. Virol.*, 60:635 (1986); and Larsson et al, *J. Virol.*, 58:600 (1986)).

The particular adenovirus serotype employed in the present invention from which the VAI gene and/or VAII gene is derived or based upon, is not critical. Examples of such adenovirus serotypes which can be employed in the present invention include those exemplified above.

As used herein, the expression "foreign gene" means any gene which encodes a foreign protein or RNA.

The foreign gene encoded and expressed by the adenovirus vectors of the present invention is not critical. By definition herein, the foreign gene is foreign to adenoviruses, but is not necessarily foreign to the target cell type which is infected by the recombinant adenovirus of the present invention.

As used herein, the expression "foreign protein" means any therapeutic protein, i.e., one which is involved in the treatment of a disease or disorder, or immunogenically protective protein antigen, which is not expressed by wild-type adenovirus.

The particular foreign protein which can be employed in the present invention is not critical thereto. The protein can be, e.g., a muscle protein, a coagulation protein, a membrane protein, a urea cycle protein or a serine protease.

Specific examples of such foreign proteins which can be employed in the present invention include dystrophin (Hoffman et al, *Cell*, 51:919 (1987)), coagulation factor VIII (Wion et al, *Nature*, 317:726 (1985)), Cystic Fibrosis Transmembrane Regulator Protein (CFTR) (Anderson et al, *Science*, 251:679 (1991); and Crawford et al, *Proc. Natl. Acad. Sci., USA*, 88:9262 (1991)), Ornithine Transcarbamylase (OTC) (Murakami et al, *J. Biol. Chem.*, 263:18437 (1988)), α1-antitrypsin (Fagerhol et al, In: Hum. Genet., Vol. 11, Harris Ed., Plenum, N.Y., p. 1 (1981)).

The genes encoding many foreign proteins are well-known in the art, and can be cloned from genomic or cDNA libraries (Sambrook et al, supra). Examples of such genes include the dystrophin gene (Lee et al, *Nature*, 349:334 (1991)), the Factor VIII gene (Toole et al, *Nature*, 312:342 (1984)), the CFTR gene (Rommens et al, *Science*, 245:1059 (1989); and Riordan et al, *Science*, 245:1066 (1989)), the OTC gene (Horwich et al, *Science*, 224:1068 (1984)), and the α1-antitrypsin gene (Lemarchand et al, *Proc. Natl. Acad. Sci., USA*, 89:6482 (1992)).

In addition, genes encoding foreign proteins such as Rb, for the treatment of vascular proliferative disorders like atherosclerosis (Chang et al, *Science*, 267:518 (1995)), and p53 for the treatment of cancer (Wills et al, *Hum. Gene Ther.*, 5:1079 (1994); Clayman et al, *Canc. Res.*, 55:1 (1995)), and HIV disease (Bridges et al, *Lancet*, 345:427 (1995)), can be employed in the present invention.

The gene transfer vector does not need to code for a functional gene product, i.e., it may also code for a partial gene product which acts as an inhibitor of a eukaryotic enzyme (Warne et al, *Nature*, 364:352–355 (1993); and Wang, *J. Cell Biochem.*, 45:49–53 (1991)).

The particular foreign RNA which can be employed in the present invention is not critical thereto. Examples of such RNAs include anti-sense RNA (Magrath, *Ann. Oncol.*, 5(Suppl 1):67–70 (1994); Milligan et al, *Ann. NY Acad. Sci.*, 716:228–241 (1994); and Schreier, *Pharma. Acta Helv.*, 68:145–159 (1994)), and catalytic RNA (Cech, *Biochem. Soc. Trans.*, 21:229–234 (1993); Cech, *Gene*, 135:33–36 (1993); Long et al, *FASE J.*, 7:25–30; and Rosi et al, *Pharm. Therap.*, 50:245–254 (1991)).

The vector of the present invention may additionally comprise a gene encoding a marker or reporter molecule to more easily trace expression of the vector.

The particular marker gene which can be employed in the present invention is not critical thereto. Examples of such marker genes which can be employed in the present invention are well-known in the art and include β-galactosidase (Fowler et al, *Proc. Natl. Acad. sci., USA*, 74:1507 (1977)), luciferase (Tu et al, *Biochem.*, 14:1970 (1975)), and chloramphenicol acetyltransferase (Gorman et al, *Mol. Cell Biol.*, 2:1044–1051 (1982)).

The vector may contain more than one gene encoding the same or different foreign proteins or RNAs. The maximum number of genes which can be present in the vector will vary depending upon the size of the individual foreign genes. Generally speaking, the total amount of DNA in the vector can be about 38 kb. Typically, the vector will contain up to 37 kb, preferably up to approximately 32 kb of DNA encoding foreign protein(s) or RNA(s). Preferably the size of the vector is smaller than the size of the adenovirus genomic DNA.

The vector may be a circular plasmid, wherein the said first adenovirus inverted terminal repeat is ligated head to head to said second adenovirus inverted terminal repeat. This can be achieved by either ligating the inverted terminal repeats head to head after isolation from adenovirus DNA or after subcloning of the inverted terminal repeats into plasmids using T4 DNA ligase (Sambrook et al, supra), or by isolating head to head ligated inverted terminal repeats from infected cells as described by Graham, *EMBO J.*, 3:2917 (1984). In this embodiment, it is preferably that a unique restriction site is present between said first adenovirus inverted terminal repeat and said second adenovirus inverted terminal repeat. Unique means that only a single cleavage site of a particular recognition sequence is present in the plasmid.

The particular unique restriction site which can be employed in the present invention is not critical thereto. Examples of such unique restriction sites which can be employed in the present invention are well-known in the art and include EagI and NotI. The restriction enzymes are commercially available, e.g., from New England Biolabs (Beverly, Mass.) or Boehringer Mannheim (Mannheim, Germany). The choice of the introduced unique restriction site varies depending on the sequence of the plasmid. Usually the introduced restriction site corresponds to a DNA sequence recognized by a rare cutting restriction enzyme.

The particular unique restriction site can be introduced between the inverted terminal repeats by DNA cloning using T4 DNA ligase (Sambrook et al, supra).

Alternatively, the vector may be a linearized plasmid. The plasmid may be linearized, e.g., by enzymatically cleaving at a unique restriction site. The inverted terminal repeats, one or both of which contains a packaging signal, may be ligated to both ends of the linearized plasmid DNA using T4 DNA ligase.

As still another alternative, a circular plasmid may be used, wherein a first restriction site and a second restriction site, which are recognized by the same restriction enzyme, are located outside of the inverted terminal repeats, i.e., the first restriction site is 5' of the first adenovirus inverted terminal repeat, and the second restriction site is 3' of the second adenovirus inverted terminal repeat, and the VAI gene and/or VAII gene, along with the foreign gene is ligated as a cassette into a unique restriction located between the first and said second adenovirus inverted terminal repeats, i.e., 3' of the first adenovirus inverted terminal repeat, and 5' of the second adenovirus inverted terminal repeat. Again, unique means that only a single cleavage site of a particular recognition sequence is present in the plasmid.

In this embodiment, the unique restriction site allows for easy replacement of one cassette containing the foreign gene, for another cassette containing a different foreign gene.

The particular restriction site which can be employed as the first and the second restriction sites in this embodiment of the present invention is not critical thereto. Examples of such restriction sites which can be employed in the present invention are well-known in the art and include PmeI. The restriction enzymes are commercially available, e.g., from New England Biolabs (Beverly, Mass.) or Boehringer Mannheim (Mannheim, Germany). The choice of the introduced first and second restriction sites varies depending on the sequence of the plasmid. Usually the introduced restriction sites correspond to a DNA sequence recognized by a rare cutting restriction enzyme.

The restrictions site can be introduced by DNA cloning using T4 DNA ligase (Sambrook et al, supra).

In this embodiment, the gene transfer vector may be linearized, and most of the plasmid-derived sequences removed from the gene transfer vector by enzymatically cleaving at the first and second restriction sites, which again are recognized by the same restriction enzyme.

The inverted terminal repeats may be either obtained directly from adenovirus DNA with or without the terminal protein attached thereto, or they may be obtained by isolation from a plasmid after subcloning of the inverted terminal repeats into plasmids (Sambrook et al, supra).

The vector of the present invention may be synthesized by DNA ligation of different DNA fragments (Sambrook et al, supra).

In another embodiment, the above-described objects of the present invention have been met by recombinant adenovirus virus particles which have encapsidated therein the gene transfer vector. The recombinant adenovirus particles are produced by the process comprising the steps of:

(1) co-transfecting or co-infecting adenovirus host cells with
   (A) adenovirus genomic DNA or adenovirus particles containing adenovirus genomic DNA, respectively, wherein said genomic DNA encodes a defective adenovirus VAI gene and/or VAII gene, and
   (B) a gene transfer vector comprising, in 5' to 3' orientation, the following elements:
      (i) a first adenovirus inverted terminal repeat,
      (ii) an adenoviral VAI gene and/or VAII gene,
      (iii) a gene foreign to adenovirus, wherein said gene is operably linked to a promoter functional in adenovirus target cells, and
      (iv) a second adenovirus inverted terminal repeat,
      wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively;

(2) harvesting adenovirus particles produced by the resulting host cells; and (3) separating, by CsCl centrifugation, adenovirus particles which have encapsidated therein said adenovirus genomic DNA from recombinant adenovirus particles which have encapsidated therein said gene transfer vector.

As used herein, the expression "recombinant adenovirus particle" means particles having an adenovirus capsid, and which contain therein the gene transfer vector instead of adenovirus genomic DNA.

As used herein, the expression "adenovirus genomic DNA" means DNA that contains all or most of the information to produce adenovirus particles. Typically, this information includes the genes that encode adenovirus functions, e.g., adenovirus DNA polymerase, penton protein, hexon protein and other viral proteins or RNAs. These function are well-known in the art (*Adenovirus DNA*, Doerfler, Ed., Martinus Nijhoff Publishing, Boston (1986)). When the DNA does not contain all of the information to produce adenovirus particles, the missing information is supplied by the adenovirus host cells.

The particular adenovirus serotype from which the adenovirus genomic DNA employed in the present invention is derived is not critical thereto. Examples of such adenovirus serotypes include those discussed above.

In a preferred embodiment, the adenovirus genomic DNA has an E1A$^-$ phenotype. More preferably, the adenovirus genomic DNA has both an E1A$^-$ phenotype and an E1B$^-$ phenotype. Most preferably, the adenovirus genomic DNA has an E1A$^-$, E1B$^-$, and E4$^-$ phenotype. Also mutations in other adenovirus functions, e.g., E2A and E3 can be present.

The E1A$^-$ phenotype is preferably the result of a deletion in the E1A region. Similarly, E1B$^-$, E2A$^-$ and E4$^-$ phenotypes are preferably the result of a deletion in the E1B, E2A and E4 regions, respectively. Adenovirus mutants containing such deletions are well-known in the art and include:

E1A$^-$: H5dl311 and H5dl312 (Jones et al, *Cell*, 13:181–188 (1978); Jones et al, *Cell*, 17:683–689 (1979); and Jones et al, *Proc. Natl. Acad. Sci., USA*, 76:3665–3669 (1979)).

E1B$^-$: H5dl313 (Jones et al, *Cell*, 17:683–689 (1979).

E2A$^-$: Zhou et al, supra.

E4$^-$: Perricaudet et al, supra; and Fines et al, supra.

In the present invention, the adenovirus genomic DNA can be engineered so that it fails to produce any VAI RNA and/or VAII RNA, or that it produces defective VAI RNA and/or VAII RNA, by either deleting parts of the VA gene(s), the complete gene(s) or important functions from the promoter region thereof.

As discussed above, adenovirus genomic DNA containing deleted VA genes cannot be amplified as a virus, and therefore must be a circular plasmid, containing the complete adenoviral genomic DNA and deleted VA genes.

More specifically, several subfragments containing the adenovirus genomic DNA may be cloned as circular plasmids using T4 DNA ligase (Sambrook et al, supra):

(1) a first plasmid may contain the left fragment of the adenovirus genomic DNA, in which unique restriction sites for BstBI and SwaI (both of which are not present in the complete adenoviral genomic DNA) are followed by adenovirus genomic DNA from nucleotide 1 up to the restriction site Bst1107I at nucleotide 5766, including a deletion in the E1 genes from nucleotide 342 up to nucleotide 3523.

(2) a second plasmid may contain a BstBI restriction site followed by adenovirus genomic DNA from the restriction site Bst1107I at nucleotide 5766 up to the BamHI restriction site at nucleotide 21562 followed by a SmaI restriction site. This subfragment contains the VA genes which, e.g., can be deleted by cleaving the DNA using the unique restriction sites SnaBI at nucleotide 10307 and BsaBI at nucleotide 11788. Both DNA ends are religated by using a short oligonucleotide containing a unique restriction site which is not present in the complete adenoviral genomic DNA, e.g., PacI. Alternatively, for deleting the promoter region of the VAI gene, a deletion can be introduced as described in the adenovirus deletion mutant dl331 (Thimmappaya et al, supra).

(3) after manipulating the VA genes in the second plasmid, a third subfragment containing the adenovirus genomic DNA from the BamHI restriction site at nucleotide 21562 up to the last nucleotide 35935 of the adenoviral genome, followed by the unique restriction site SwaI, may be ligated to the second plasmid.

With the plasmids produced in (1), (2) and (3), a new circular plasmid containing the complete adenoviral genomic DNA with an E1$^-$ phenotype can be produced. More specifically, by using the restriction sites Bst1107I and BstBI, a subfragment from the plasmid produced in (1) can be introduced into the plasmid produced in (2) after it has been cleaved with Bst11071 and BstBI. This new plasmid DNA is cleaved with BstBI and PacI, and the resulting subfragment ligated into the plasmid produced in (3), which has been cleaved with BstBI and PacI.

To produce adenoviral genomic DNA with additional E2A$^-$, E3$^-$ and/or E4$^-$ phenotype, defective packaging signal and/or enlarged size, specific deletions or additional DNA may be introduced into the corresponding subfragments cloned as circular plasmids. As described above, the subfragments may then be used to obtain a new circular plasmid containing the complete adenoviral genomic DNA with the desired specific phenotype.

For co-transfection with gene transfer vector, the adenoviral genomic DNA cloned as circular plasmid must be linearized by cleaving at the unique restriction sites SwaI. These specific sites are located at both sites of the inverted terminal repeats of the adenovirus genomic DNA.

The adenovirus host cells are those which are used to propagate the claimed adenovirus vectors in vitro, and are permissive for adenovirus growth.

The particular adenovirus host cells which can be employed in the present invention are not critical thereto. Examples of such adenovirus host cells which can be employed in the present invention are well-known in the art and include human 293 cells (a human embryonic kidney cell line that constitutively produces E1 proteins) (Graham et al, *Virol.*, 52:456 (1973)). currently this is the only available cell line providing the E1 function. Other examples of adenovirus host cells include HeLa (ATCC CCL 2) and the KB cell line (ATTC CCL 17).

It is required when using adenovirus genomic DNA which has an E1$^-$ phenotype, that in the adenovirus host cells, adenoviral E1 proteins are expressed. This is because the E1 functions are required for viral propagation. Human 293 cells are an example of such adenovirus E1$^+$ host cells.

Co-transfection of adenovirus host cells can be carried out by well-known methods, such as the calcium phosphate transfection procedure, as described by Graham et al, *Virol.*, 52:456–467 (1973), or using lipofectamine (Gibco BRL, Gaithersburg, Md.).

The ratio of adenovirus genomic DNA to gene transfer vector employed in the co-transfection/co-infection step is not critical to the present invention, and may vary depending upon the method used for transfection. Generally, the weight ratio will be about 1 to 1.

Harvesting of the adenovirus particles produced by the co-transfected/co-infected host cells can be carried out by well-known methods, such as resuspension of the cells in phosphate buffered saline (PBS) containing 5–10% (v/v) glycerol, followed by preparation of a cell extract by freezing and thawing of the cells, as described by Mitani et al, supra.

After co-transfection/co-infection of the adenovirus host cells, the cell monolayer is generally either:

(a) overlayed with 0.5% (w/v) agarose containing medium for about 3 to 10 days until individual viral plaques appear representing infected cells. Individual plaque isolates are then analyzed for the presence of the foreign DNA having the inverted terminal repeats with the packaging signal within viral particles, for example, by the polymerase chain (PCR) reaction using forward and reverse primers homologous to the foreign gene present in the gene transfer vector; or (b) not overlayed with agarose. After the cell monolayer is completely lysed, the virus is harvested, and analyzed for the presence of the foreign DNA in virus particles, e.g., by PCR.

Method (a) is preferable because by directly isolating individual plaque isolates it is easier to propagate a uniform and clonal recombinant adenovirus isolate.

If the gene transfer vector contains a marker gene, e.g., β-galactosidase, it is also possible to stain the monolayer by adding an additional overlay containing substrate for the protein encoding by the marker gene, e.g., 0. 01% (w/v) 5-bromo-4-chloro-3-indolyl β-D-galactoside (X-gal).

Both methods (a) and (b) lead to a mixed virus population consisting of (i) the recombinant adenovirus particles and (ii) adenovirus particles containing adenovirus genomic DNA. All of the protein functions, except for VAI and VAII, which are necessary for the replication and packaging of the foreign DNA into virus particles, as well as all other viral proteins, like the capsid proteins, are encoded by the adenovirus genomic DNA in this system.

After this step, the mixed virus population is serially passaged, e.g., about 4–8 times, in adenovirus host cells in order to increase the number of recombinant virus particles.

The adenovirus particles which have encapsidated therein the adenovirus genomic DNA can be separated from recombinant adenovirus particles which have encapsidated therein the gene transfer vector by CsCl centrifugation. For example, after serial passage on adenovirus host cells, the infected cells are collected by centrifugation in a cell centrifuge (Beckmann) at 400×g, and then the cells are resuspended in PBS containing 5–10% (v/v) glycerol. A cell extract is prepared by freezing the resuspended cells three times in liquid nitrogen, or alternatively, in a ethanol/dry ice bath, and thawing at 37° C. After spinning down the cell debris at 1000×g, the resulting cell extract is subjected to equilibrium centrifugation in a 50% (w/v) CsCl gradient. For every 1.0 ml of cell extract, 0.5 g of CsCl is dissolved therein. A total volume of 10 ml can be subjected to ultracentrifugation in SW41 ultracentrifugation tubes (Beckmann) in a SW41 rotor (Beckmann) at 32,000 rpm (175,587×g at $r_{max}$) for more than 16 hr at 4° C.

It was surprisingly found in the present invention that approximately an equal amount of recombinant adenovirus particles to adenovirus particles containing adenovirus genomic DNA are produced after the co-transfection/co-infection. As a result, the number of serial passages can be significantly reduced upon separation of the adenovirus particles containing adenovirus genomic DNA and the recombinant adenovirus particles after CsCl centrifugation.

It is not clear why an approximately equal amount of recombinant adenovirus particles to adenovirus particles containing adenovirus genomic DNA are produced after the co-transfection/co-infection. However, it is believed that such occurs because both types of adenoviral particles are incapable of producing new infectious particles by themselves which have encapsidated the vector or genomic DNA, respectively. To produce new viral particles, recombinant adenovirus particles need trans-complementing functions from the adenovirus genomic DNA (viral functions for replicating viral DNA and viral capsid proteins), and adenovirus genomic particles need trans-complementing functions from the recombinant adenovirus particles (VA functions).

After CsCl centrifugation, the recombinant adenovirus particles can be dialyzed against PBS or Tris-buffered saline to remove the CsCl, and stored at −20 to −80° C. prior to use.

Alternatively, the recombinant adenovirus particles of the present invention can be lyophilized, and then stored prior to use at −20 to −80° C. The recombinant adenovirus particles can then be reconstituted with water or a physiological solution or medium prior to use.

With the currently available vectors, it is believed that expression of viral proteins within the infected cells stimulates a cellular immune response of the host against the infected cells, resulting in only transient expression of the foreign gene. However, in the present invention, all of the viral genes encoding adenovirus proteins are preferably substituted by the foreign DNA in the recombinant adenovirus particles. Thus, it is expected that the immunogenicity of the recombinant adenovirus particles is considerably reduced or abolished, and the problem of transient expression of the foreign gene can be overcome.

In yet still another embodiment, the above-described objects of the present invention have been met by a method for introducing and expressing a foreign gene in adenovirus target cells comprising infecting said target cells with the above recombinant adenovirus particles which have encapsidated therein the gene transfer vector.

Infection can be carried out in vitro or in vivo. In vitro infection of cells is performed by adding recombinant adenovirus particles to the cell culture medium. When infection is carried out in vivo, the solution containing the recombinant adenovirus particles may be administered by a variety of modes, depending on the tissue which is to be infected. Examples of such modes of administration include injection of recombinant adenovirus particles into the arterial or venous vascular system, injection of recombinant adenovirus particles directly into a tissue (e.g., liver, brain or muscle), direct application to a surface (e.g., skin or bladder), or instillation into an organ (e.g., lung or gastrointestinal tract).

Adenovirus target cells are those to be infected in vivo to achieve a therapeutic or immunological effect, and are permissive for adenovirus growth.

The particular adenovirus target cell to be infected in the present invention is not critical. Examples of such adenovirus target cells include liver cells, muscle cells, lung cells, and tumor cells. The cells may be derived from any animal, e.g., mammals, such as humans, as well as avian species.

The capacity of the gene transfer vector for DNA is large. Thus, other elements can be included in the gene transfer element, e.g., promoters, cell specific enhancer sequences, a hormone responsive element, mammalian artificial chromosome elements or elements from the autonomous replicating circular minichromosomes, elements that can be regulated by chemical substances or "stuffer DNA".

The particular tissue specific promoters employed is not critical to the present invention.

Viral or mammalian promoters are suitable to achieve expression of the foreign protein. For example, the SV40 promoter and the cytomegalovirus promoter (Andersson et al, *J. Biol. Chem.*, 264:8222–8229 (1989)) will result in a constitutive high-level expression of the foreign protein in the infected cells; and the human t-PA gene promotor (Fisher et al, *J. Biol. Chem.*, 260:11223–11230 (1985)) will result in expression of the foreign protein in a well-known regulated manner. By employing a promotor with well-known properties, the pattern of expression of the foreign protein following infection of a target cell population can be optimized.

Selection of a promotor which is active in only a specific cell-type will enhance tissue-specific expression of a foreign gene. For example, use of the MCK promoter will lead to expression in skeletal and cardiac muscle, but not in liver tissue. Additional examples of tissue specific promoters include, but are not limited to, α S1- and β-casein promoters which are specific for mammary tissue (Platenburg et al, *Trans. Res.*, 3:99–108 (1994); and Maga et al, *Trans. Res.*, 3:36–42 (1994)); the phosphoenolpyruvate carboxykinase promoter which is active in liver, kidney, adipose, jejunum and mammary tissue (McGrane et al, *J. Reprod. Fert.*, 41:17–23 (1990)); the tyrosinase promoter which is active in lung and spleen cells, but not testes, brain, heart, liver or kidney (Vile et al, *Canc. Res.*, 54:6228–6234 (1994)); the involucerin promoter which is only active in differentiating keratinocytes of the squamous epithelia (Carroll et al, *J. Cell Sci.*, 103:925–930 (1992)); and the uteroglobin promoter which is active in lung and endometrium (Helftenbein et al, *Annal. N.Y. Acad. Sci.*, 622:69–79 (1991)).

Alternatively, cell specific enhancer sequences can be used to control expression, for example human neurotropic papovirus JCV enhancer regulates viral transcription in glial cells alone (Remenick et al, *J. Virol.*, 65:5641–5646 (1991)). Yet another way to control tissue specific expression is to use a hormone responsive element (HRE) to specify which cell lineages a promoter will be active in, e.g., the MMTV promoter requires the binding of a hormone receptor, such as progesterone receptor, to an upstream HRE before it is activated (Beato, *FASEB J.*, 5:2044–2051 (1991); and Truss et al, *J. Steroid Biochem. Mol. Biol.*, 41:241–248 (1992)).

Additional genetic elements may be included on the gene transfer vector in order to modify its behavior inside the recipient animal cell (Hodgson, *Bio/Technology*, 13:222–225 (1995)). Such elements include, but are not limited to, mammalian artificial chromosome elements or elements from the autonomous replicating circular minichromosomes, such as found in DiFi colorectal cancer cells, to allow stable non-integrated retention of the expression cassette (Huxley et al, *Bio/Technology*, 12:586–590 (1994); and Untawale et al, *Canc. Res.*, 53:1630–1636 (1993)), intergrase to direct integration of the expression cassette into the recipient cells chromosome (Bushman, *Proc. Natl. Acad. Sci., USA*, 91:9233–9237 (1994), the inverted repeats from adeno-associated virus to promote non-homologous integration into the recipient cells chromosome (Goodman et al, *Blood*, 84:1492–1500 (1994), recA or a restriction enzyme to promote homologous recombination (PCT Patent Publication No. WO9322443 (1993); and PCT Patent Publication No. WO9323534-A (1993)), elements that direct nuclear targeting of the eukaryotic expression cassette (Hodgson, supra; and Lewin, *Genes V*, Oxford University Press, Oxford (1994)), or elements that can be regulated by chemical substances, e.g., tetracycline responsive elements that can mediate reversible transcriptional activation or repression of gene activity upon administration or withdrawal of tetracycline (Furth, *Proc. Natl. Acad. Sci., USA*, 91:9302–9306 (1992)).

It is preferable that the total size of the DNA inserted into the vector of the present invention be is about 28–32 kb of DNA. This is because adenoviral vectors need to have a minimum size to be stably propagated (Parks et al, *J. Virol.*, 71:3293–3298 (1997)). Thus, when the size of the foreign gene insert, including the any additional genetic elements, if present, e.g., promoters, cell specific enhancer sequences, a hormone responsive element, mammalian artificial chromosome elements or elements from the autonomous replicating circular minichromosomes, and elements that can be regulated by chemical substances discussed above, is less than about 28–32 kb, it is preferable to include within the vector "stuffer DNA".

For example, the stuffer DNA may be DNA derived from prokaryotic or eukaryotic genomic DNA. Preferably, the stuffer DNA is derived from noncoding genomic regions. More preferably, the stuffer DNA is derived from noncoding human genomic DNA.

However, it is preferable that the stuffer DNA contains at least one matrix association region (MAR) Sykes et al, *Mol. Gen. Genet.*, 212:301–309 (1988)). Inclusion of a MAR sequence in the vector is believed to confer nuclear stability to the vector, and to be important in achieving high expression levels.

Polynucleosomes are constrained into loops or domains, and are insulated from the effects of chromatin structure and torsional strain from flanking domains by the cross-complexation of MARs, and matrix proteins. MARs have an average size of 500 bp, are spaced about every 30 kb, and are control elements maintaining independent realms of gene activity. A fraction of MARs may cohabit with core origins of replication (ORIs), and another fraction might cohabit with transcriptional enhancers. DNA replication, transcription, repair, splicing, and recombination seem to take place on the nuclear matrix. Classical AT-rich MARs have been proposed to anchor the core enhancers, and core origins complexed with low abundancy transcription factors to the nuclear matrix via the cooperative binding to MARs of abundant classical matrix proteins (topoisomerase II, histone H1, lamins, SP120, ARBP, SATB1); this creates a unique nuclear microenvironment rich in regulatory proteins able to sustain transcription, replication, repair, and recombination (Boulikas, *International Review of Cytology*, 162A:279–388 (1995)).

An example of stuffer DNA containing a MAR sequence is the HPRT gene (Ewards et al, *Genomics*, 6:593–608 (1990)), particularly nucleotides 5534–6107 thereof (Sykes et al, *Mol. Gen. Genet.*, 212:301–309 (1988)).

The following examples are provided for illustrative purposes only, and are in no way intended to limit the scope of the present invention.

EXAMPLE 1

Preparation of Vector STK99

Vector STK99, which contains adenovirus genomic DNA having deletions in the VA genes, the E1-genes and the packaging signal, was prepared as follows:

A double-stranded oligodeoxynucleotide with the restriction sites AscI-AvrII-FseI-PacI was generated by annealing single-stranded oligodeoxynucleotides #17302: 5'-GGCGCGCCCCTAGGGGCCGGCCTTAATTAA-3' (SEQ ID NO:3); and #17303: 5'-TTAATTAAGGCCGGCCCCTAGGGGCGCGCC-3' (SEQ ID NO:4). The oligonucleotides were produced by chemical synthesis (Sambrook et al, *In: Molecular Cloning. A Laboratory Manual*, Cold Spring Harbor Laboratory Press (1989)).

More specifically, 3.0 μg of each of #17302 and #17303 were incubated with 60 μl of H₂O at 65° C. for 5 min, and were then allowed to slowly cool down to room temperature. The annealed oligodeoxynucleotide was inserted into the EcoRV site of Bluescript KSII (Stratagene) using T4 DNA ligase. That is, 1.8 μg of Bluescript II KS was digested with EcoRV. Then, 100 ng of the resulting digested DNA was ligated to 1.0 ng of the annealed oligonucleotide in a volume of 10 μl in the presence of 0.1 mM ATP and T4 DNA ligase, followed by transformation of DH5α competent bacterial cells (GibcoBRL). The resulting plasmid was called pSTK2.

Then, 1.0 μg of pSTK2 was digested with BstXI, and the cleavage site was made blunt-end using Klenow enzyme, as described by Sambrook et al, supra.

More specifically, 1.0 μg of STK2 DNA was incubated at 55° C. in a volume of 30 μl with 10 units of BstXI. Then, 0.3 μl of 10 mM dNTPs and 1 unit of T4 DNA polymerase was added, and the reaction was allowed to proceed at 12° C. for 20 min. Next, in order to end the enzymatic reaction, 1.5 μl of 0.5 M EDTA was added, followed by incubation at 65° C. for 10 min, followed by phenol/chloroform extraction and ethanol precipitation.

Next, a double-stranded oligodeoxynucleotide with the restriction sites SwaI-PmeI-SnaBI was generated by annealing single-stranded oligodeoxynucleotides #17300: 5'-ATTTAAATGCCCGCCCGTTTAAACTACGTA-3' (SEQ ID NO:5); and #17301: 5'-TACGTAGTTTAAACGGGCGGGCATTTAAAT-3' (SEQ ID NO:6) following the procedure as described above.

Then, 80 ng of the resulting digested pSTK2 was ligated to 5.0 ng of the resulting doubled-stranded oligonucleotide, using T4 DNA ligase in the presence of 0.1 mM ATP, followed by transformation of competent bacterial DH5α cells. The resulting plasmid was called pSTK3.

A second SwaI-PmeI-SnaBI oligodeoxynucleotide was then inserted into the ApaI site of STK3.

More specifically, 1.2 μg of STK3 DNA was cleaved with 3 units of ApaI in a volume of 50 μl. Next, the DNA was made blunt-end by adding 0.3 μl of 10 mM dNTPs and 1 unit T4 DNA polymerase. Then, the reaction was inactivated by adding 2.0 μl of 0.5 M EDTA and incubating at 65° C. for 15 min, followed by phenol extraction and ethanol precipitation. Next, the cleaved DNA was dephosphorylated by adding 0.8 units of shrimp alkaline phosphatase. After incubation for 2.5 hrs, the phosphatase was inactivated by incubation at 65° C. for 5 min, followed by phenol extraction and ethanol precipitation.

Then, a double-stranded oligodeoxynucleotide with the restriction sites SwaI-PmeI-SnaBI was generated by annealing single-stranded oligodeoxynucleotides #17300 and #17301 following the procedure as described above. The resulting oligodeoxynucleotide was inserted into the blunt-ended ApaI site of STK3 using T4 DNA ligase.

More specifically, 6.0 ng of annealed oligodeoxynucleotide was ligated to 100 ng of ApaI cleaved and blunt-ended STK3 DNA by incubation with 400 units of T4 DNA ligase in the presence of 0.1 mM ATP, followed by transformation of competent bacterial DH5α cells. The resulting plasmid was called STK5.

Then, a BstBI-Bst1107I-BamHI-SwaI oligodeoxynucleotide was inserted into the SnaBI sites of STK5.

More specifically, 3.3 μg of STK5 DNA was cleaved with 6 units of SnaBI in a volume of 60 μl for 8 hrs. Next, the cleaved DNA was dephosphorylated as described above, followed by phenol extraction and ethanol precipitation, as described above.

Then, single-stranded oligodeoxynucleotides #24129: 5'-TTCGAACTAATCGAGTATACATTCGTAGGGATCC GATGTCGATTTAAAT-3' (SEQ ID NO:7); and #24130: 5'-ATTTAAATCGGACATCGGATCCCTACGAATGTATA CTCGATTAGTTCGAA-3' (SEQ ID NO:8), were annealed by incubating 3.0 μg of each oligodeoxynucleotide in a volume of 60 μl at 70° C. for 5 min, and the reaction was allowed to slowly cool down to room temperature.

Next, 100 ng of cleaved STK5 DNA was incubated with 0.8 ng of annealed and double-stranded oligodeoxynucleotide in the presence of 0.1 mM ATP and 400 units of T4 DNA ligase. Then, the ligation mixture was used to transform XL-2 blue cells (Stratagene Cloning Systems; La Jolla, Calif.). The resulting plasmid was called STK5-24129.

Then, the 16 kb Bst1107I/BamHI fragment of Ad5 genomic DNA containing the VAI and VAII genes was inserted into STK5-24129.

More specifically, 3.0 μg of Ad5 DNA was cleaved with 12 units of BamHI and 12 units of Bst1107I in a volume of 60 μl, followed by phenol extraction and ethanol precipitation. BamHI cleaves at nt. 21562 of Ad5 DNA and Bst1107I cleaves at nt. 5766 of Ad5 DNA.

Then, 3.3 μg of STK5-24129 DNA was cleaved with 10 units of Bst1107I and 10 units of BamHI in a volume of 100

μl. Next, the DNA was phosphorylated, as described above, followed by phenol extraction and ethanol precipitation.

Next, 100 ng of the BamHI-Bst1107I cleaved STK5-24129 DNA was incubated together with approximately 100 ng of BamHI-Bst1107I cleaved Ad5 DNA in the presence of 1.0 mM ATP and 200 units of T4 DNA ligase. The ligation mixture was used to transform competent XL-2 blue cells. Recombinant colonies were identified by colony hybridization (Maniatis, *In: Molecular Cloning. A Laboratory Manual*, Cold Spring Harbor Laboratory Press (1989)), using, as the hybridization probe, a 1.1 kb DNA fragment that contains the VAI region of Ad5 and that had previously been isolated from Ad5 DNA. The resulting plasmid that contained the 16 kb DNA fragment from Ad5 was called STK43.

Next, a deletion mutation was introduced into the VAI and VAII genes.

More specifically, 3.0 μg of STK43 DNA was cleaved with 12 units of SnaBI at 37° C., followed by an additional cleavage with 10 units of BsaBI at 60° C. in a volume of 60 μl. SnaBI cleaves at nt. 10307 of Ad5 DNA and BsaBI cleaves at nt. 11788 of Ad5 DNA. Then, the DNA was dephosphorylated, as described above, followed by phenol extraction and ethanol precipitation.

Next, a BsaBI site containing oligodeoxynucleotide was inserted into STK3.

More specifically, 3.3 μg of STK3 DNA was cleaved with 10 units of SmaI in a volume of 60 μl. Next, the cleaved DNA was dephosphorylated with calf intestinal phosphatase, followed by phenol extraction and ethanol precipitation.

Then, single-stranded oligodeoxynucleotides #23681: 5'-GGATAAACATCCCC-3' (5'-phosphorylated) (SEQ ID NO:9); and # 23682: 5'-GGGGATGTTTATCC-3' (5'-phosphorylated) (SEQ ID NO:10) were annealed as described above.

Next, 100 ng of SmaI cleaved STK3 DNA, prepared as described above, was incubated with 2.5 ng of annealed oligonucleotide in the presence of 0.1 mM ATP and 400 units of T4 DNA ligase. Then, the ligation mixture was used to transform XL-2 blue competent cells. Clones containing the oligodeoxynucleotide were identified by restriction analysis using BsaBI. One positive clone (clone #5) was used for DNA preparation using the Qiagen Midi kit.

Next, the 1481 bp DNA Ad5 DNA fragment containing the VAI and VAII genes was inserted into STK3 containing the additional BsaBI site (clone #5).

More specifically, 3.0 μg of clone #5 DNA was cleaved with 8 units of SnaBI and 10 units of BsaBI in a volume of 60 μl. Then, the DNA was dephosphorylated, followed by phenol extraction and ethanol precipitation, as described above.

3.5 μg of Ad5 DNA was cleaved with 8 units of SnaBI and 10 units of BsaBI in a volume of 60 μl, followed by phenol extraction and ethanol precipitation. Then, 100 ng of cleaved clone #5 DNA, prepared as described above, was incubated together with 50 ng of the cleaved Ad5 DNA in the presence of 0.2 mM ATP and 200 units of T4 DNA ligase. Next, this ligation reaction was used to transform XL-2 blue competent cells. 10 colonies were analyzed by restriction analysis. One colony gave the expected restriction pattern. This plasmid DNA was used for further experimentation and was called STK3xBsaBI/Ad5-SnaBI/BsaBI (1481 bp). This plasmid was used to introduce a deletion into the VAI and VAII genes.

More specifically, a polymerase chain reaction (PCR) was performed using 100 ng of STK3xBsaBI/Ad5-SnaBI/BsaBI DNA, 400 ng each of oligodeoxynucleotides #24132: 5'-TTAA<u>CCGGACTGCGGCGAACGG</u>-3' (5'-phosphorylated) (SEQ ID NO:11) (underlined: Ad5 nt. 10951–10968; and bold: 1/2 PacI site); and #24133: 5'-TTAA<u>TTTTCCGCCATGATACCCTTGCGA</u>-3' (5'-phosphorylated) (SEQ ID NO:12) (underlined: Ad5 nt.10669–10650; and bold: 1/2 PacI site); and PFU polymerase (Stratagene). The PCR profile was: 15 cycles with denaturation at 94° C. for 1 min, annealing at 50° C. for 2 min, and extension at 72° C. for 3 min. After the PCR, the PCR product was purified by phenol extraction and ethanol precipitation. Next, the resulting DNA fragment of approximately 3.8 kb was purified by agarose gel electrophoresis and electroelution. Then, the DNA fragment was circularized by incubation with T4 DNA ligase and 0.1 mM ATP, thus generating a new PacI site. Next, the ligation mixture was used to transform XL-2 blue competent cells. Recombinant clones were identified by restriction analysis. One clone (clone #54) was used for further experimentation and was called PCRΔVA.

Next, the SnaBI-BsaBI DNA fragment of plasmid PCRΔVA, containing the deleted VAI and VAII genes, was inserted into the SnaBI and BsaBI sites of plasmid STK43 by replacing the original SnaBI-BsaBI DNA fragment containing the VAI and VAII genes.

More specifically, 4.0 μg of PCRΔVA DNA was cleaved with 16 units of SnaBI and 10 units of BsaBI in a volume of 80 μl. Then, the resulting fragment was purified by agarose gel electrophoresis and electroelution.

Next, 100 ng of cleaved STK43 DNA, prepared as described above, was incubated with 20 ng of the purified SnaBI/BsaBI cleaved PCRΔVA product in the presence of 0.1 mM ATP and 200 units of T4 DNA ligase. The ligation mixture was used to transform XL-2 blue competent cells. Individual clones were analyzed by restriction analysis with SnaBI and BsaBI. Several clones carried the deletion mutation of the VAI and VAII genes, one of which (clone #18) was used in the further experiments. This plasmid, containing the 16 kb BamHI/Bst1107I fragment of Ad5 with the deletion mutation of the VAI and VAII genes, was called STK46.

Next, the right BamHI fragment of Ad5 was cloned into Bluescript KSII by first cleaving of Ad5 DNA with BamHI, then an oligodeoxynucleotide that contained a BamHI site was ligated to the right terminus, and finally, the right terminus was cloned into the BamHI site of Bluescript KSII. BamHI cleaves at nt. 21562 of Ad5 DNA.

More specifically, 3.5 μg of Bluescript KSII DNA was cleaved with 12 units of BamHI in a total volume of 60 μl. Then, the DNA was dephosphorylated, followed by phenol extraction and ethanol precipitation, as described above.

Next, an oligodeoxynucleotide containing SwaI-BamHI sites was ligated to the right terminus of Ad5 DNA.

More specifically, in order to remove the terminal peptides of the terminal protein, 5.0 μg of Ad5 DNA was incubated with NaOH at a final concentration of 0.3 M for 90 min at 37° C. Then, the reaction was neutralized by adding of hydrochloric acid to 0.3 M and Tris (pH 8.0) to 50 mM. Next, for re-annealing, the reaction was incubated at 65° C. for 90 min, after which the reaction was allowed to slowly cool down to room temperature. Then, single-stranded oligodeoxynucleotides 123546: 5'-CGGCGGATCCATTTAAAT-3' (SEQ ID NO:13) (bold: SwaI site; and italic: BamHI site); and 1 23547:

5'-ATTTAAATGGATCCGCC-3' (SEQ ID NO:14) (bold: SwaI site; and italic: BamHI site), that contain a SwaI and a BamHI site were annealed as described above. Next, 200 ng of the double-stranded oligodeoxynucleotides were incubated together with Ad5 DNA that had been treated as described above, in the presence of 0.1 M ATP and 4000 units of T4 DNA ligase in a total volume of 200 µl. After ligation, the ligated DNA was purified by phenol extraction and ethanol precipitation. Next, the DNA was cleaved with 24 units of SalI and 20 units of BamHI in a total volume of 200 µl, followed by phenol extraction and ethanol precipitation. Then, the right terminus, containing the ligated SwaI-BamHI oligonucleotide, was purified by agarose gel electrophoresis and electroelution. Next, 100 ng of the BamHI cleaved Bluescript KSII DNA was ligated to approximately 100 ng of the right adenoviral terminus that was prepared as described above in the presence of 1.0 mM ATP and 200 units of T4 DNA ligase. Then, the ligation mixture was used to transform XL-2 blue competent bacterial cells. This plasmid was called STK80.

Next, the Ad5 DNA fragment contained in STK80 was cloned into STK46, thus generating a plasmid with the adenoviral genome from bp 5766 to the right terminus containing a deletion-mutation of the VAI and VAII genes.

More specifically, 3.5 µg of STK46 DNA was cleaved with 20 units of BamHI in a total volume of 70 µl. Then, the cleaved DNA was dephosphorylated, followed by phenol extraction and ethanol precipitation, as described above.

Next, 4.0 µg of STK80 DNA was cleaved with 20 units of BamHI in a total volume of 80 µl. Then, the BamHI fragment of STK80 was purified by agarose gel electrophoresis and electroelution. The fragment was further purified using a Qiagen tip 5 column and following the procedure recommended by the manufacturer for DNA purification using buffers QBT for binding, QC for washing, and QF for elution.

Next, 100 ng of STK46 DNA cleaved with BamHI, as described above, was incubated together with approximately 100 ng of the BamHI fragment of STK80, purified as described above, in the presence of 1.0 nM ATP and 200 units of T4 DNA ligase. The ligation mixture was used to transform XL-2 competent bacterial cells. Recombinant clones were identified by colony hybridization, and confirmed by restriction analysis. Several clones showed the correct restriction pattern, and one clone (#27) was used for further experimentation. This plasmid was called STK84.

Then, plasmid STK61 was generated by inserting a 4597 bp EcoRV DNA fragment of bacteriophage lambda into the EcoRV site of plasmid pΔE1sp1B (Microbix Biosystems Inc.; Ontario, Canada). Plasmid pΔE1sp1B contains the left terminus of Ad5.

More specifically, the 4597 bp EcoRV fragment from bacteriophage lambda (bp. 2086–6683) was isolated by cleavage of bacteriophage lambda DNA, followed by agarose gel electrophoresis and electroelution. Then, the fragment was cloned into the EcoRV site of the dephosphorylated pΔE1sp1B DNA. This plasmid was called STK61.

Next, 3.0 µg of STK61 DNA was cleaved with 20 units of HindIII and SspI in a volume of 200 µl. Then, the DNA was made blunt-end using 2 units of the Klenow fragment of DNA polymerase I, followed by It phenol extraction and ethanol precipitation. Next, the cleaved DNA was dephosphorylated using calf intestinal phosphatase, followed by phenol extraction and ethanol precipitation, as described above.

In order to introduce additional flanking restriction sites at the left end of the Ad5 DNA, the inverted terminal repeat and the packaging signal of the pΔE1sp1B plasmid were removed and a left terminus generated by PCR was introduced.

More specifically, the left terminus of Ad5 was amplified by PCR from 20 ng of Ad5 DNA using oligodeoxynucleotides #25438: 5'-TTCGAATTTAAAT CATCATCAATAATATACCTTATTTTG-3' (5' phosphorylated) (SEQ ID NO:15) (underlined: Ad5 ITR (1–26); bold: SwaI site; and italic: BstBI site); and #23540: 5-TGATCTAGACGCTATGAGTAACACAAA-3' (SEQ ID NO:16) (underlined: Ad5 nt. 335–318; and bold: XbaI site), under the same PCR conditions as described above using PFU polymerase. #25438 encompasses nucleotides 1–26 of Ad5, and contains, in addition, 5' BstBI and SwaI sites. #23540 encompasses nucleotides 335–318 of Ad5, and contains, in addition, a 5' XbaI site.

Next, approximately 20 ng of the PCR product described above was ligated into 100 ng of the cleaved STK61 DNA in the presence of 0.1 mM ATP and 200 units of T4 DNA ligase. Then, the ligation mixture was used to transform XL-2 blue competent bacterial cells. Recombinant clones were identified by colony hybridization using the above-described PCR product as a probe, and confirmed by restriction analysis. Several clones showed the correct restriction pattern, and one clone (#12) was used for further experimentation. This plasmid was called STK87.

Next, the Bst1107I-BstBI fragment of STK87 was is cloned into STK46.

More specifically, 3.0 µg of STK87 DNA was cleaved with 15 units of Bst1107I and 10 units of BstBI in total volumes of 60 µl, followed by phenol extraction and ethanol precipitation. Then, the Bst1107I-BstBI fragment was purified by agarose gel electrophoresis and electroelution.

Next, 2.0 µg of STK46 DNA was cleaved with 10 units of Bst1107I and 10 units of BstBI in a total volume of 60 µl. Then, the DNA was dephosphorylated using calf intestinal phosphatase, followed by phenol extraction and ethanol precipitation, as described above. Next, about 100 ng of the purified Bst1107I-BstBI fragment was ligated to 100 ng of the STK46 DNA in the presence of 1.0 mM ATP and 400 units of T4 DNA ligase. Then, the ligation reaction was used to transform XL-2 blue competent bacterial cells. Recombinant clones were identified by colony hybridization using the above-described fragment as a probe; and confirmed by restriction analysis. Several clones showed the correct restriction pattern, and one clone (#21) was used for further experimentation. This plasmid was called STK95.

Next, the PacI-BstBI fragment of STK95 was cloned into the PacI and BstBI sites of STK84.

More specifically, 5.0 Mg of STK95 DNA was cleaved with 20 units of Pacd and BstBI in a total volume of 100 µl. Then, then PacI-BstBI fragment was purified by agarose gel electrophoresis and electroelution.

Next, 3.0 µg of STK84 DNA was cleaved with 15 units of PacI and BstBI in a total volume of 60 µl. Then, the DNA was dephosphorylated using calf intestinal phosphatase, followed by phenol extraction and ethanol precipitation, as described above.

Then, 100 ng of cleaved STK84 DNA was incubated with about 100 ng of the purified PacI-BstBI fragment derived from STK95 in the presence of 1.0 mM ATP and 400 units of T4 DNA ligase. Next, the ligation reaction was used to transform XL-2 blue competent bacterial cells. Recombinant clones were identified by colony hybridization, and confirmed by restriction analysis. Several clones showed the correct restriction pattern, and one clone (#59) was used for further experimentation. This plasmid was called STK99.

EXAMPLE 2

Preparation of Gene Transfer Vector STK110

Gene transfer vector STK110, which contains the Ad2 VA genes, 8.8 kb from the human HPRT gene locus and the human $\alpha_1$-antitrypsin gene locus, was prepared as follows:

The left terminus of Ad5 was amplified by PCR using oligodeoxynucleotides #23531: 5'-AGCTTTGTTTAAA CATCATCAATAATATACCTTATTTTG-3' (SEQ ID NO:17) (bold: PmeI restriction site; and underlined: Ad5 (bp 1–26)); and #23532: 5'-CGATAAGCTTGATATC AAAACGCCAACTTTGACCC-3' (SEQ ID NO:18) (bold: HindIII restriction site; italic: EcoRV restriction site; and underlined: Ad5 (bp 440–421)).

More specifically, 10 ng of Ad5 DNA was subjected to PCR by using 400 ng of each oligodeoxynucleotide #23531 and #23532, DNTP (final concentration 200 μM) and 1.25 units of PFU polymerase in a volume of 50 μl. The PCR conditions were: 94° C. for 1 min, 50° C. for 2 min, 72° C. for 3 min; 15 cycles total followed by a single 72° C. extension for 10 min. The resulting PCR product was cleaved with PmeI and HindIII.

More specifically, 20 μl of the PCR reaction was incubated with 4 units of PmeI and 4 units of HindIII in a reaction volume of 50 μl, followed by phenol/chloroform extraction and ethanol precipitation.

Then, STK3, prepared as described in Example 1 above, was cleaved with PmeI and HindIII and the PmeI/HindIII cleaved PCR product, generated as described above, was inserted into the PmeI and HindIII sites of STK3 using T4 DNA ligase under the ligation conditions as described above. The resulting plasmid was called STK31.

Next, the VAI gene of Ad2 was inserted into STK31. More specifically, 3.0 μg of STK31 DNA was cleaved with 11 units of EcoRV in a total volume of 60 μl. Then, the ends of the cleaved DNA were dephosphorylated with calf intestinal phosphatase (CIP) as described above. Next, the DNA was purified by phenol/chloroform extraction and ethanol precipitation.

3.4 μg of plasmid pVAI+II (Juettermann et al, *J. Virol.*, 65:1735 (1991)), which contains the VAI and VAII genes of Ad2, was cleaved with 10 units of HincII and 9 units of MscI. HincII cleaves 5' of the VAI gene within the polylinker of the plasmid, and MscI cleaves 3' of the VAI gene. Then, the HincII-MscI fragment was purified by agarose gel electrophoresis and electroelution.

Next, 100 ng of the isolated HincII-MscI fragment were incubated together with 100 ng of EcoRV cleaved STK31 DNA in the presence of 0.1 mM ATP and 400 units of T4 DNA ligase. The ligation reaction was used to transform XL-2-blue competent bacterial cells. Positive clones were identified by colony hybridization using the VAI gene containing DNA fragment as hybridization probe. The resulting plasmid was called STK31xVA.

Then, the right terminus of Ad5 was amplified by PCR using oligodeoxynucleotides #23531 and #24147: 5'-CGATAAGCTTGATATCACTCCGCCCTAAAACCTACG-3' (SEQ ID NO:19) (bold: HindIII restriction site; italic: EcoRV restriction site; and underlined: Ad5 (bp 35818–35837)), under the same PCR conditions as described above. The resulting PCR product was cleaved with PmeI and HindIII.

STK3 was cleaved with PmeI and HindIII and the PmeI/ HindIII cleaved PCR product described above was inserted into the PmeI/HindIII site of the cleaved STK3 using T4 DNA ligase. The resulting plasmid was called STK3-23531/ 24147

Then, STK31xVA was cleaved with EcoO109I. The EcoO109I site was made blunt-end using Klenow fragment of DNA polymerase I.

More specifically, 3.5 μg of STK31xVA DNA was incubated with 10 units of EcoO109I in a volume of 60 μl at 37° C. for 3 hrs. Then, the cleaved DNA was made blunt-end by incubation together with dNTP's (80 μM final concentration), and the Klenow fragment of DNA polymerase I for 20 min at room temperature, followed by phenol/chloroform extraction and ethanol precipitation.

Then, plasmid STK3-23531/24147 was cleaved with SnaBI and EcoRV under standard conditions. The resulting SnaBI-EcoRV fragment containing the right terminus of Ad5 was purified by gel-electrophoresis and electroelution, and was inserted into the EcoO109I site of STK31xVA.

More specifically, 20 ng of the purified DNA fragment was incubated with 100 ng of cleaved STK31xVA DNA in the presence of 0.1 mNM ATP and 200 units of T4 DNA ligase. The resulting plasmid was called STK44.

A cosmid containing part of the hypoxanthine guanine phosphoribosyltransferase (HPRT) gene (U72D8) (Edwards et al, *Genomics*, 6:593 (1990)) was cleaved with EcoRI and BamHI. EcoRI cleaves at bp 10609 and BamHI at bp 1777 of the sequence that is deposited in the GenBank-database (Locus: Human HPRT gene [EHUMHPRTB]; gb:humhprtb).

More specifically, 1.0 μg of the cosmid DNA was cleaved with 5 units of EcoRI and BamHI, followed by phenol/ chloroform extraction and ethanol precipitation.

Then, STK3 was cleaved with EcoRI and BamHI and was dephosphorylated.

More specifically, 3.0 μg of STK3 DNA was cleaved with 15 units each of EcoRI and BamHI in a volume of 60 μl at 37° C. for 4 hrs. Then, 5 units of CIP were added and the reaction was allowed to proceed for 1 hr. Next, 0.5 μl of 0.5 M EDTA was added, and the CIP was inactivated by incubation at 65° C. for 1 hr, followed by phenol/chloroform extraction and ethanol precipitation.

Then, the 8832 bp EcoRI/BamHI HPRT DNA fragment was inserted into the EcoRI/BamHI sites of STK3 using T4 DNA ligase.

More specifically, 100 ng of cleaved STK3 DNA was incubated with 70 ng of cleaved cosmid DNA in the presence of 0.5 mM ATP and T4 DNA ligase at room temperature. Then, the ligation mixture was used to transform XL-1 blue competent cells. HPRT DNA containing colonies were identified using colony hybridization, using as the probe a, 3.7 kb internal HPRT HindIII fragment that had been isolated by gel purification and electroelution. The resulting plasmid was called STK77.

Then, STK44 was cleaved with HincII.

More specifically, 3.5 μg of STK44 DNA was cleaved with HincII in a volume of 60 $A^1$ at 37° C., followed by dephosphorylation with CIP as described above, phenol/ chloroform extraction and ethanol precipitation.

Then, STK77 was cleaved with BamHI and SalI. More specifically, 5.0 μg of STK77 DNA was cleaved with 20 units of BamHI in a volume of 100 μl at 37° C. for 4 hrs. The ends of the cleaved DNA were made blunt-end by adding 0.5 μl of 10 mM DNTP and 5 units of the Klenow fragment of DNA polymerase I. Then, the BamHI/SalI HPRT fragment was purified by gel electrophoresis and electroelution. Next, the BamHI/SalI HPRT fragment was cloned into the HincII site of STK44 using T4 DNA ligase as described above.

The ligation mixture was used to transform XL-2 blue cells. Positive recombinants were identified using standard colony hybridization using the 3.7 kb HPRT HindIII fragment described above as a probe. The resulting plasmid was called STK52.

Then, STK52 DNA was cleaved with EcoRI.

More specifically, 5.0 µg of STK52 DNA was cleaved with EcoRI in a total volume of 50 µl. Then, the ends of the cleaved DNA were made blunt-end using dNTPs and the Klenow fragment of DNA polymerase I. Next, the DNA was purified by phenol extraction and ethanol precipitation. Then, the DNA was dephosphorylated with CIP as described above, followed by phenol/chloroform extraction and ethanol precipitation.

STK45-AT#10 DNA is a plasmid that contains a 19 kb SalI fragment encompassing the human $\alpha_1$-antitrypsin gene locus. This fragment includes the endogenous promoters, all exons and introns and the endogenous polyadenylation signal and was derived from bacteriophage lambda aNN containing the normal human $\alpha_1$-antitrypsin allele (Dycaico et al, Science, 2,42:1409–1412 (1988)). The 19 kb SalI fragment was released from STK45-AT#10 by cleavage of 5.0 µg of DNA with 25 units of SalI in a total volume of 50 µl. Next, the cleaved DNA was made blunt-end as described above. The 19 kb fragment was further purified by gel-electrophoresis and electroelution. Then, the 19 kb fragment was inserted into the EcoRI site of STK52.

More specifically, approximately 100 ng of the purified 19 kb fragment was incubated with 100 ng of EcoRI cleaved and blunt-end STK52 DNA with T4 DNA ligase in the presence of 1.0 ml ATP in a total volume of 10 µl. Next, the ligation mixture was used to transform XL-2 blue cells. Positive clones were identified by colony hybridization using the 19 kb SalI fragment as a probe. The resulting plasmid was called STK110.

EXAMPLE 3

Rescue of Gene Transfer Vector STK110

STK110 DNA and STK99 DNA were co-transfected into 293 cells. After several days individual plaques were isolated and the plaque isolates were used for further propagation.

More specifically, 20 µg of STK110 DNA were cleaved with 100 units of SwaI in a total volume of 200 µl at 25° C. Then, the DNA was purified by phenol extraction and ethanol precipitation. After centrifugation, the DNA was dissolved at a concentration of 0.5 µg/ml in TE buffer.

In addition, 20 µg of STK99 DNA were cleaved with 120 units of PmeI in a total volume of 200 µl at 37° C. Then, the DNA was purified by phenol extraction and ethanol precipitation. After centrifugation, the DNA was dissolved at a concentration of 0.5 µg/ml in TE buffer.

Next, the cleaved STK110 and STK99 DNAs were used for transfection of 293 cells.

More specifically, 15 µl of STK99 DNA and 8.0 µl of STK110 DNA were mixed with 267 µl of serum-free MEM medium (GibcoBRL) to give a total volume of 300 µl. Then, 12 µl Lipofectamin (GibcoBRL) was mixed with 288 µl serum-free MEM medium to give a total volume of 300 µl. Next, both solutions were mixed and were left at room temperature for 30 min. Then, 2.4 µl of serum-free MEM medium was added and the combined 3.0 µl were used to overlay subconfluent 293 cells in 60 mm cell culture dishes. After 5 hrs incubation at 37° C. 95% humidity/5% $CO_2$, 1.2 ml of MEM medium containing 20% (v/v) fetal calf serum was added. The 293 cells were incubated for additional 24 hrs before the cells were overlayed with agarose containing MEM medium with 5.0% (v/v) bovine calf serum and antibiotics in standard concentrations (GibcoBRL).

After 9 days, plaques were isolated and were added to 1.5 ml tubes containing 300 µl 10 mM Tris (pH 7.5) and 10% (v/v) glycerol.

Next, 9 µl of 5.0 M NaCl was added to the plaques to make the solution isotonic. Then, $1.0 \times 10^4$ 293 cells that had been plated the day before in 48-well cell culture dishes were infected with 100 µl of the primary plaque isolate. 160 hrs after infection, when a full cytopathic effect was apparent, the cells were harvested in 10 mM Tris (pH 7.5) and 10% (v/v) glycerol in a volume of 500 µl. One of the isolates was called ΔVA41(10-15-96).

Then, $5.0 \times 10^4$ 293 cells, plated in 24-well cell culture dishes the day before, were infected with 150 µl of ΔVA41 (10-15-96). The cells were harvested 48 hrs after infection, at which point a full cytopathic effect was apparent, in 500 pl of 10 mM Tris (pH 7.5) and 10% (v/v) glycerol. This preparation was called ΔVA41(10-15-96/10-17-96).

Next, the cells were subjected 3 times to freeze/thawing. Then, $5.0 \times 10^5$ 293 cells that had been plated the day before in 6 well cell culture dishes, were infected with 300 µl of ΔVA41(10-15-96/10-17-96). The cells were harvested 120 hrs after infection, when a full cytopathic effect was apparent, in 500 µl of 10 mM Tris (pH 7.5) and 10% (v/v) glycerol. This preparation was called ΔVA41(10-17-96/1-23-97).

Next, the cells were subjected 3 times to freeze/thawing. Then, $1.0 \times 10^6$ 293 cells that had been plated the day before in 60 mm cell culture dishes, were infected with 200 µl of ΔVA41(10-17-96/1-23-97). The cells were harvested 120 hrs after infection, when a full cytopathic effect was apparent, in 500 µl of 10 mM Tris (pH 7.5) and 10% (v/v) glycerol. This preparation was called ΔVA41(1-23-97/1-30-97).

Then, DNA was prepared from ΔVA41(10-17-96/1-23-97) and from ΔVA41(1-23-97/1-30-97). More specifically, cell lysates were prepared by 3 times freezing and thawing of the cells. Then, the extract was subjected to centrifugation. Next, the pellet was resuspended in 300 µl of TE buffer. Then, 30 µl of Proteinase K (5.0 mg/ml in water), 30 µl of 10% (w/v) SDS and 14 µl of 0.5 M EDTA was added. The reaction was incubated overnight at 37° C. Then, the DNA was purified by phenol extraction and ethanol precipitation.

Next, the DNA was subjected to restriction analysis by cleavage with HindIII and XhoI.

More specifically, 1.0 1 µg of DNA was digested with either 10 units of HindIII or 10 units of XhoI in a total volume of 20 µl at 37° C. Then, the DNA was separated by gel electrophoresis in a 0.8% (w/v) agarose gel. The DNA was stained by including 0.5 µl of ethidium bromide (10 mg/ml) in the agarose gel.

Upon analysis of the agarose gel it was apparent that in the DNA from the ΔVA41(10-17-96/1-23-97) preparation very high and aproximal equal amounts of AdSTK99 and AdSTK110 DNA were present. In DNA from 30 the ΔVA41 (1-23-97/1-30-97) preparation even more AdSTK110 DNA was present. In control experiments, in which the helper virus contained the VAI and VAII genes and the vector did not carry a VAI gene, only helper virus DNA was detected at this passage, and no vector DNA was visible upon ethidium bromide staining at this level of sensitivity. Based upon these results it is clear that a system based on trans-complementation between the VAI gene containing vector and the helper virus that has a deletion of both the VAI and VAII genes results in an amount of vector compared to helper virus that is estimated to be at least 100-fold higher when compared to the conventional system that does not take advantage of a trans-complementation of the VAI functions between vector and helper virus.

To test if the above-described vector expresses the $\alpha_1$-antitrypsin gene locus, 50 μl of ΔVA41(1-23-97/1-30-97) was added to subconfluent mouse liver cells in 60 mm cell culture dishes. After 1 hr of incubation at 37° C., 95% humidity/5% $CO_2$, the virus was removed and 5.0 ml of MEM medium containing 10% (v/v) fetal calf serum was added. The infected cells were incubated for an additional 48 hrs, and 0.25 ml of medium was removed to measure the amount of secreted $\alpha_1$-antitrypsin using an enzyme-linked immunosorbent assay (ELISA) (Kay et al, *Hum. Gene Ther.*, 3:641 (1992); and Morral et al, *Hum. Gene Ther.*, 8:1275 (1997)). The total amount of secreted $\alpha_1$-antitrypsin was found to be 668 ng per 1,000,000 cells in 24 hrs.

While the invention has been described in detail, and with reference to specific embodiments thereof, it will be apparent to one of ordinary skill in the art that various changes and modifications can be made therein without departing from the spirit and scope thereof.

What is claimed:

1. A gene transfer vector consisting essentially of, in 5' to 3' orientation, the following elements:
   (i) a first adenovirus inverted terminal repeat,
   (ii) an adenoviral VAI gene and/or VAII gene,
   (iii) a gene foreign to adenovirus, wherein said gene is operably linked to a promoter functional in adenovirus target cells, and
   (iv) a second adenovirus inverted terminal repeat,
wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively.

2. The vector of claim 1, wherein both element (i) and element (iv) additionally comprise an adenovirus packaging signal.

3. The vector of claim 1, wherein said vector additionally comprises a gene encoding a marker.

4. The vector of claim 1, wherein said vector additionally comprises a matrix associated region.

5. The vector of claim 1, wherein said vector is a circular plasmid, and said first adenovirus inverted terminal repeat is ligated to said second adenovirus inverted terminal repeat to form said circular plasmid.

6. The vector of claim 5, wherein a unique restriction site is present between said first adenovirus inverted terminal repeat and said second adenovirus inverted terminal repeat.

7. The vector of claim 1, wherein said vector is a linearized plasmid.

8. The vector of claim 1, wherein said foreign gene encodes for a protein selected from the group consisting of dystrophin, coagulation factor VII, cystic fibrosis transmembrane regulator protein, ornithine transcarbamylase, α1-antitrypsin, Rb, and p53.

9. A recombinant adenovirus virus particle which has encapsidated therein a gene transfer vector consisting essentially of, in 5' to 3' orientation, the following elements:
   (i) a first adenovirus inverted terminal repeat,
   (ii) an adenoviral VAI gene and/or VAII gene,
   (iii) a gene foreign to adenovirus, wherein said gene is operably linked to a promoter functional in adenovirus target cells, and
   (iv) a second adenovirus inverted terminal repeat,
wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively.

10. The recombinant adenovirus virus particle of claim 9, wherein both element (i) and element (iv) additionally comprise an adenovirus packaging signal.

11. The recombinant adenovirus virus particle of claim 9, wherein said vector additionally comprises a gene encoding a marker.

12. The recombinant adenovirus virus particle of claim 9, wherein said vector additionally comprises a matrix associated region.

13. The recombinant adenovirus virus particle of claim 9, wherein said vector is a circular plasmid, and said first adenovirus inverted terminal repeat is ligated to said second adenovirus inverted terminal repeat to form said circular plasmid.

14. The recombinant adenovirus virus particle of claim 13, wherein a unique restriction site is present between said first adenovirus inverted terminal repeat and said second adenovirus inverted terminal repeat.

15. The recombinant adenovirus virus particle of claim 9, wherein said vector is a linearized plasmid.

16. The recombinant adenovirus virus particle of claim 9, wherein said foreign gene encodes for a protein selected from the group consisting of dystrophin, coagulation factor VII, cystic fibrosis transmembrane regulator protein, ornithine transcarbamylase, α1-antitrypsin, Rb, and p53.

17. A method for the production of recombinant adenovirus particles comprising the steps of:
   (1) co-transfecting or co-infecting adenovirus host cells with
      (A) adenovirus genomic DNA or adenovirus particles containing adenovirus genomic DNA, respectively, wherein said genomic DNA encodes a defective adenovirus VAI gene and/or VAII gene, and
      (B) a gene transfer vector consisting essentially of, in 5' to 3' orientation, the following elements:
         (i) a first adenovirus inverted terminal repeat,
         (ii) an adenoviral VAI gene and/or VAII gene,
         (iii) a gene foreign to adenovirus, wherein said gene is operably linked to a promoter functional in adenovirus target cells, and
         (iv) a second adenovirus inverted terminal repeat,
      wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively;

(2) harvesting adenovirus particles produced by the resulting host cells; and (3) separating, by CsCl centrifugation, adenovirus particles which have encapsidated therein said adenovirus genomic DNA from recombinant adenovirus particles which have encapsidated therein said gene transfer vector.

18. The method of claim 17, wherein said adenovirus genomic DNA has an E1A⁻ phenotype.

19. The method of claim 18, wherein said adenovirus genomic DNA also has at least one of an E1B⁻ phenotype, an E2A⁻ phenotype, an E3⁻ phenotype, and an E4⁻ phenotype.

20. The method of claim 17, wherein said adenovirus genomic DNA has a defective packaging signal.

21. The method of claim 17, wherein said adenovirus host cells express adenovirus E1 proteins.

22. The method of claim 17, wherein both element (i) and element (iii) additionally comprise an adenovirus packaging signal.

23. The method of claim 17, wherein said vector additionally comprises a gene encoding a marker.

24. The method of claim 17, wherein said vector additionally comprises a matrix associated region.

25. The method of claim 17, wherein said vector is a circular plasmid, and said first adenovirus inverted terminal repeat is ligated to said second adenovirus inverted terminal repeat to form said circular plasmid.

26. The method of claim 25, wherein a unique restriction site is present between said first adenovirus inverted terminal repeat and said second adenovirus inverted terminal repeat.

27. The method of claim 26, wherein said vector is a linearized plasmid.

28. The method of claim 17, wherein said foreign gene encodes for a protein selected from the group consisting of dystrophin, coagulation factor VII, cystic fibrosis transmembrane regulator protein, ornithine transcarbamylase, α1-antitrypsin, Rb, and p53.

29. A method for introducing and expressing a foreign gene in adenovirus target cells comprising infecting said adenovirus target cells with a recombinant adenovirus particle which has encapsidated therein a gene transfer vector consisting essentially of, in 5' to 3' orientation, the following elements:

(i) a first adenovirus inverted terminal repeat, (ii) an adenoviral VAI gene and/or VAII gene, (iii) a gene foreign to adenovirus, wherein said gene is operably linked to a promoter functional in adenovirus target cells, and (iv) a second adenovirus inverted terminal repeat, wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively.

30. The method of claim 29, wherein both element (i) and element (iii) additionally comprise an adenovirus packaging signal.

31. The method of claim 29, wherein said vector additionally comprises a gene encoding a marker.

32. The method of claim 29, wherein said vector additionally comprises a matrix associated region.

33. The method of claim 29, wherein said vector is a circular plasmid, and said first adenovirus inverted terminal repeat is ligated to said second adenovirus inverted terminal repeat to form said circular plasmid.

34. The method of claim 33, wherein a unique restriction site is present between said first adenovirus inverted terminal repeat and said second adenovirus inverted terminal repeat.

35. The method of claim 29, wherein said vector is a linearized plasmid.

36. The method of claim 29, wherein said foreign gene encodes for a protein selected from the group consisting of dystrophin, coagulation factor VII, cystic fibrosis transmembrane regulator protein, ornithine transcarbamylase, α1-antitrypsin, Rb, and p53.

* * * * *